US012419684B2

(12) United States Patent
Yang et al.

(10) Patent No.: US 12,419,684 B2
(45) Date of Patent: Sep. 23, 2025

(54) SYSTEMS AND METHODS FOR CALIBRATING LASER PULSES

(71) Applicant: Boston Scientific Scimed, Inc., Maple Grove, MN (US)

(72) Inventors: Baocheng Yang, Fremont, CA (US); David Pih, Milpitas, CA (US); Xirong Yang, Fremont, CA (US); Peter Bull, San Jose, CA (US); Brian Cheng, San Jose, CA (US); Rongwei Jason Xuan, Fremont, CA (US); Jian James Zhang, Lancaster, MA (US); Thomas Charles Hasenberg, Campbell, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 641 days.

(21) Appl. No.: 17/664,306

(22) Filed: May 20, 2022

(65) Prior Publication Data

US 2022/0376459 A1    Nov. 24, 2022

Related U.S. Application Data

(60) Provisional application No. 63/191,546, filed on May 21, 2021.

(51) Int. Cl.
*H01S 3/06* (2006.01)
*A61B 18/00* (2006.01)
(Continued)

(52) U.S. Cl.
CPC .............. *A61B 18/20* (2013.01); *H01S 3/061* (2013.01); *H01S 3/10069* (2013.01);
(Continued)

(58) Field of Classification Search
CPC .......... A61B 18/20–28; A61B 2018/2005–266; H01S 3/10069; H01S 5/0617
See application file for complete search history.

(56) References Cited

U.S. PATENT DOCUMENTS

| | | | |
|---|---|---|---|
| 6,353,623 B1 * | 3/2002 | Munks ................. | H01S 5/0687 372/38.07 |
| 6,526,071 B1 * | 2/2003 | Zorabedian ............ | H01S 5/141 372/98 |

(Continued)

FOREIGN PATENT DOCUMENTS

| | | | | |
|---|---|---|---|---|
| CN | 106532429 A | * | 3/2017 | ........... H01S 5/0021 |
| GB | 2425881 A | * | 11/2006 | ........... H01S 5/0612 |

(Continued)

OTHER PUBLICATIONS

International Search Report and Written Opinion for International Application No. PCT/US2022/072473 mailed Sep. 6, 2022.

*Primary Examiner* — Joshua King
(74) *Attorney, Agent, or Firm* — Seager, Tufte & Wickhem, LLP

(57) ABSTRACT

A medical laser system for outputting laser pulses includes at least one laser cavity configured to generate at least one laser pulse, a rotating mirror configured to receive and reflect the at least one laser pulse, a beam splitter configured to receive and reflect a portion of the at least one laser pulse received from the rotating mirror, an energy-sensing device configured to detect the portion of the at least one laser pulse, an energy measurement assembly configured to generate a measurement signal based on the portion of the at least one laser pulse detected by the energy-sensing device, and a controller. The controller may include a calibration module. The calibration module may be configured to generate at least one categorized calibration table, determine calibration parameters, interpolate the calibration param- (Continued)

eters, and cause the at least one laser cavity to generate at least one calibrated laser pulse.

13 Claims, 7 Drawing Sheets

(51) Int. Cl.
    *A61B 18/20*      (2006.01)
    *H01S 3/10*      (2006.01)
    *H01S 3/13*      (2006.01)
    *H01S 3/16*      (2006.01)

(52) U.S. Cl.
    CPC ............ *H01S 3/1305* (2013.01); *H01S 3/161* (2013.01); *H01S 3/1616* (2013.01); *H01S 3/1623* (2013.01); *H01S 3/1643* (2013.01); *A61B 2018/00779* (2013.01)

(56) References Cited

U.S. PATENT DOCUMENTS

| | | | | |
|---|---|---|---|---|
| 8,605,764 | B1* | 12/2013 | Rothaar | G03B 21/2033 |
| | | | | 372/29.01 |
| 2001/0050083 | A1* | 12/2001 | Marchitto | A61B 5/150351 |
| | | | | 128/898 |
| 2002/0041611 | A1* | 4/2002 | May | H01S 5/0687 |
| | | | | 372/18 |
| 2002/0043616 | A1* | 4/2002 | May | H01S 5/0687 |
| | | | | 250/226 |
| 2002/0044575 | A1* | 4/2002 | May | H01S 5/0687 |
| | | | | 372/20 |
| 2003/0036751 | A1* | 2/2003 | Anderson | A61B 5/0059 |
| | | | | 606/9 |
| 2003/0147442 | A1* | 8/2003 | Larson | H01S 5/06256 |
| | | | | 372/50.11 |
| 2003/0152390 | A1* | 8/2003 | Stewart | H04B 10/40 |
| | | | | 398/22 |
| 2004/0165624 | A1* | 8/2004 | Stewart | H04B 10/572 |
| | | | | 372/32 |
| 2004/0213306 | A1* | 10/2004 | Fennema | H01S 5/141 |
| | | | | 372/38.01 |
| 2006/0072631 | A1* | 4/2006 | Farrell | H01S 5/062 |
| | | | | 372/20 |
| 2006/0108510 | A1* | 5/2006 | Draper | H01S 5/06804 |
| | | | | 250/214.1 |
| 2007/0213697 | A1* | 9/2007 | Holliday | A61F 9/008 |
| | | | | 606/5 |
| 2009/0299693 | A1* | 12/2009 | Kane | H01S 3/0014 |
| | | | | 702/179 |
| 2011/0044366 | A1* | 2/2011 | Bainbridge | H01S 5/06812 |
| | | | | 372/46.01 |
| 2012/0138586 | A1* | 6/2012 | Webster | B23K 15/08 |
| | | | | 219/121.64 |
| 2013/0223461 | A1* | 8/2013 | Ensher | H01S 5/06256 |
| | | | | 372/38.02 |
| 2013/0243015 | A1* | 9/2013 | Eriksson | H01S 5/0014 |
| | | | | 372/20 |
| 2015/0141972 | A1* | 5/2015 | Woodley | A61F 9/00804 |
| | | | | 606/5 |
| 2016/0011056 | A1* | 1/2016 | Liu | G01J 1/0228 |
| | | | | 250/338.1 |
| 2018/0109066 | A1* | 4/2018 | Cannon | H01S 3/1312 |
| 2019/0221998 | A1* | 7/2019 | Nishita | H01S 5/0687 |
| 2020/0052464 | A1* | 2/2020 | Champion | H01S 5/06808 |
| 2020/0280169 | A1* | 9/2020 | Blazo | H01S 5/125 |

FOREIGN PATENT DOCUMENTS

| | | | | |
|---|---|---|---|---|
| WO | WO-2011031977 | A1 * | 3/2011 | ............ A61K 33/00 |
| WO | WO-2012031580 | A2 * | 3/2012 | ........... B23K 26/705 |
| WO | 2015148462 | A1 | 10/2015 | |

* cited by examiner

SYSTEMS AND METHODS FOR CALIBRATING LASER PULSES

CROSS-REFERENCE TO RELATED APPLICATIONS

This application claims the benefit of priority from U.S. Provisional Application No. 63/191,546, filed on May 21, 2021, which is incorporated by reference herein in its entirety.

TECHNICAL FIELD

The present disclosure generally relates to medical/surgical laser systems, and more particularly, to systems and methods for calibrating laser pulses with such systems.

BACKGROUND

Medical laser systems are used for a variety of surgical procedures. These procedures may include dusting and/or fragmentation of stones in the kidney, the bladder, and/or the ureter. Medical laser systems are also used to create incisions and to ablate and/or coagulate soft tissues, such as, but not limited to, the prostate. Medical laser systems may output laser pulses having variable characteristics, such as the average power of the output laser pulses, based on preset conditions. For example, a laser pulse having a specific average power level may be generated based on one or more input parameters, such as pulse energy and/or pulse repetition frequency. However, laser pulses at each preset average power level need to be calibrated in order to ensure the accuracy of the output laser pulses.

A medical laser system capable of outputting a large number of laser pulse modes (e.g., pulse shapes, pulse repetition frequency, pulse output power levels, etc.) may require multiple laser cavities to generate the various laser pulse modes. To ensure accuracy, the lasing performance of each of the multiple laser cavities should be calibrated for every available laser pulse mode of the medical laser system. However, calibrating multiple laser cavities for every available laser pulse mode may be inefficient and time-consuming.

SUMMARY OF THE DISCLOSURE

Examples of the disclosure relate to, among other things, systems and methods for calibrating laser pulses, among other aspects. Each of the examples disclosed herein may include one or more of the features described in connection with any of the other disclosed aspects.

In one example, a medical laser system may be provided for outputting laser pulses. The medical laser system may include: at least one laser cavity configured to generate at least one laser pulse; a rotating mirror configured to receive and reflect the at least one laser pulse; a beam splitter configured to receive and reflect a portion of the at least one laser pulse received from the rotating mirror; an energy-sensing device configured to detect the portion of the at least one laser pulse; an energy measurement assembly configured to generate a measurement signal based on the portion of the at least one laser pulse detected by the energy-sensing device; and a controller comprising a calibration module configured to: generate at least one categorized calibration table based on a spectrum matrix; determine calibration parameters for the at least one categorized calibration table based on the measurement signal; interpolate the calibration parameters of the at least one categorized calibration table; and cause the at least one laser cavity to generate at least one calibrated laser pulse based on the at least one categorized calibration table with interpolated calibration parameters.

In other aspects, a medical laser system described herein may include one or more of the following features. The controller may further include a memory comprising the spectrum matrix and the categorized calibration table. The at least one categorized calibration table may be generated based on one or more laser pulse modes. The one more laser pulse modes may include at least one of a regular-low pulse mode, a short-low pulse mode, a long-low pulse mode, a regular-medium pulse mode, a short-medium pulse mode, a long-medium pulse mode, a short-high pulse mode, a long-high pulse mode, a dust pulse mode, or a burst pulse mode. The calibration parameters of the at least one categorized calibration table may be interpolated based on a Newtonian interpolation algorithm. The calibration parameters may include at least one of a target energy measurement value or a pulse width value of the at least one laser pulse. The at least one laser pulse may be generated by one of the at least one laser cavity. Interpolated calibration parameters of the at least one categorization calibration table may be transferred to another categorization calibration table associated with another one of the at least one laser cavity. The calibration module may be further configured to interpolate the calibration parameters of the at least one categorized calibration table based on one or more laser pulse energy levels and one or more laser pulse repetition rates. The calibration module may be further configured to: compare the calibration parameters to a predetermined accuracy threshold; and determine whether the calibration parameters satisfy the predetermined accuracy threshold. The calibration module may be further configured to: upon determining the calibration parameters does not satisfy the predetermined accuracy threshold, adjusting the at least one of the calibration parameters; and comparing the at least one of the calibration parameters to the predetermined accuracy threshold. The at least one laser cavity may include four laser cavities. Each of the at least one laser cavity may include a glass plate arranged at a Brewster Angle. The beam splitter may include a polarization-insensitive coating.

In another example, a method of calibrating a laser system may be provided. The method may include: generating at least one laser pulse from at least one laser cavity; detecting a portion of the at least one laser pulse; generating a measurement signal based on the portion of the at least one laser pulse; generating at least one categorized calibration table based on a spectrum matrix; determining calibration parameters for the at least one categorized calibration table based on the measurement signal; interpolating the calibration parameters of the at least one categorized calibration table; and generating at least one calibrated laser pulse based on the at least one categorized calibration table with interpolated calibration parameters.

In other aspects, a method of calibrating a laser system described herein may include one or more of the following features. The at least one categorized calibration table may be generated based on one or more laser pulse modes. The one more laser pulse modes may include at least one of a regular-low pulse mode, a short-low pulse mode, a long-low pulse mode, a regular-medium pulse mode, a short-medium pulse mode, a long-medium pulse mode, a short-high pulse mode, a long-high pulse mode, a dust pulse mode, or a burst pulse mode. The calibration parameters of the at least one categorized calibration table may be interpolated based on a Newtonian interpolation algorithm. The calibration parameters may include at least one of a target energy measurement value or a pulse width value of the at least one laser pulse. The at least one laser pulse may be generated by one of the at least one laser cavity. The method may further include transferring the interpolated calibration parameters of the at least one categorization calibration table to another categorization calibration table associated with another one of the at least one laser cavity. The method may further include interpolating the calibration parameters of the at least one categorized calibration table based on one or more laser pulse energy levels and one or more laser pulse repetition rates. The method may further include: comparing the calibration parameters to a predetermined accuracy threshold; determining whether the calibration parameters satisfies the predetermined accuracy threshold; upon determining the calibration parameters does not satisfy the predetermined accuracy threshold, adjusting the at least one of the calibration parameters; and comparing the at least one of the calibration parameters to the predetermined accuracy threshold.

In yet another example, a non-transitory computer-readable medium may store instructions for calibrating laser pulses of a medical laser system, the instructions, when executed by one or more processors, may cause the one or more processors to perform operations. The operations may include: generating at least one laser pulse from at least one laser cavity; detecting a portion of the at least one laser pulse; generating a measurement signal based on the portion of the at least one laser pulse; generating at least one categorized calibration table based on a spectrum matrix; determining calibration parameters for the at least one categorized calibration table based on the measurement signal; interpolating the calibration parameters of the at least one categorized calibration table; and generating at least one calibrated laser pulse based on the at least completed calibration table with interpolated calibration parameters.

BRIEF DESCRIPTION OF THE DRAWINGS

The accompanying drawings, which are incorporated in and constitute a part of this specification, illustrate various exemplary embodiments and, together with the description, serve to explain the principles of the disclosed embodiments.

DETAILED DESCRIPTION

Figure 1:
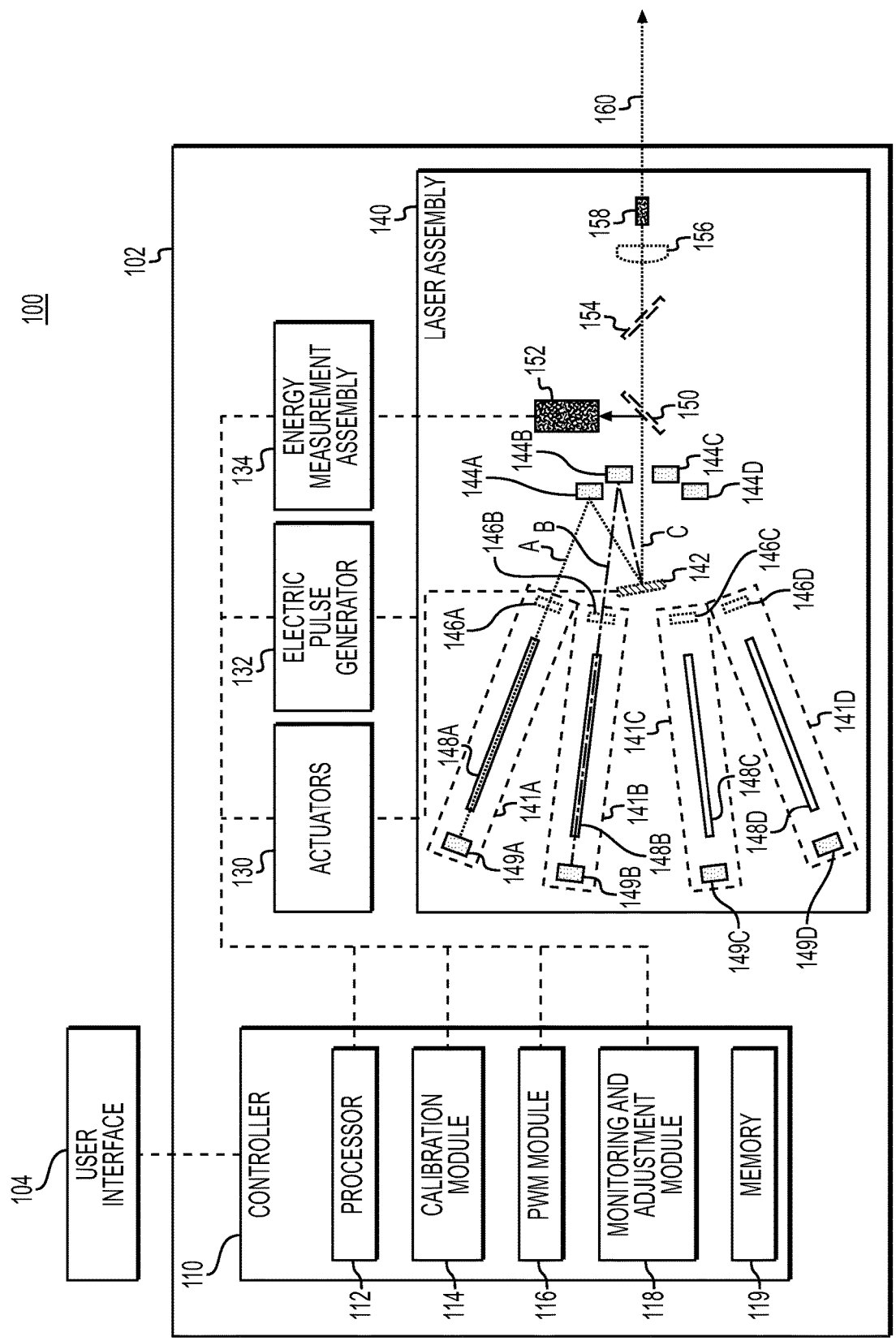
FIG. 1 is a schematic of a medical laser system according to an exemplary embodiment.

Both the foregoing general description and the following detailed description are exemplary and explanatory only and are not restrictive of the features, as claimed. As used herein, the terms "comprises," "comprising," "having," "including," or other variations thereof are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

For ease of description, portions of the disclosed devices and/or their components are referred to as proximal and distal portions. It should be noted that the term "proximal" is intended to refer to portions closer to a laser cavity of the laser system, and the term "distal" is used herein to refer to portions further away from the laser cavity of the laser system, e.g., toward an end of a laser fiber that outputs a laser pulse. Similarly, extends "distally" indicates that a component extends in a distal direction, and extends "proximally" indicates that a component extends in a proximal direction. Additionally, terms that indicate the geometric shape of a component/surface refer to exact and approximate shapes.

Examples of this disclosure may be used to calibrate, monitor, and/or adjust laser pulses having one or more pulse modes (or shapes) generated by one or more laser cavities of a medical laser system. In some embodiments, the medical laser system may include at least one laser cavity configured to generate at least one laser pulse and a rotating mirror configured to receive and reflect at least one laser pulse. Further, the medical laser system may include a beam splitter configured to receive and reflect a portion of at least one laser pulse received from the rotating mirror. In some embodiments, the medical laser system may include an energy-sensing device configured to detect the portion of at least one laser pulse. Further, the medical laser system may include an energy measurement assembly configured to generate a measurement signal based on the portion of at least one laser pulse detected by the energy pulse sensor. The medical laser system may include a controller configured to calibrate at least one laser pulse based on the measurement signal received from the energy measurement assembly. In one embodiment, at least one laser pulse may be calibrated by determining at least one target laser parameter based on the measurement signal. Further, at least one laser pulse may be calibrated by interpolating at least one target laser parameter based on at least one categorized spectrum matrix. Furthermore, a calibrated laser pulse may be generated based on at least one interpolated target laser parameter.

Examples of the disclosure may relate to systems, devices, and methods for performing various medical procedures and/or treating target features, such as tissues of a subject (e.g., a patient). Reference will now be made in detail to examples of the disclosure described above and illustrated in the accompanying drawings. Wherever possible, the same reference numbers will be used throughout the drawings to refer to the same or like parts.

FIG. 1 shows a schematic depiction of an exemplary medical laser system 100 in accordance with an example of this disclosure. The medical laser system 100 may include a laser chassis 102 and a user interface 104. The laser chassis 102 may include a controller 110, actuators 130, an electric pulse generator 132, an energy measurement assembly 134, and a laser assembly 140. The user interface 104 may be communicatively coupled to the controller 110 by, for example, a wired connection, wireless connection, and the like. It should be appreciated that, in some embodiments, the user interface 104 may be a device integral with the medical laser system 100, and in other embodiments, the user interface 104 may be a remote device in communication (e.g., wireless, wired, etc.) with the medical laser system 100. The user interface 104 may include input and output ports to connect with input and output devices such as keyboards, mice, touchscreens, monitors, displays, etc., to receive user inputs and output messages thereon.

Still referring to FIG. 1, the controller 110 may be communicatively coupled to the laser assembly 140 directly or indirectly via the actuators 130, electric pulse generator 132, and/or the energy measurement assembly 134 by, for example, a wired connection, a wireless connection, and the like. In some examples, the controller 110 may be a computer system incorporating a plurality of hardware components that allow the controller 110 to receive data (e.g., laser input parameter data, laser sensor data, etc.), process information (e.g., calibration logic or algorithm, PWM scheme logic or algorithm, monitoring, and adjustment logic or algorithm, etc.), and/or generate control signals to generate and output laser pulses via the laser assembly 140. Illustrative hardware components of the controller 110 may include at least one processor 112, at least one calibration module 114, at least one pulse width modulation (PWM) module 116, at least one monitoring and adjustment module 118, and at least one memory 119.

The processor 112, the calibration module 114, the PWM module 116, and the monitoring and adjustment module 118 of the controller 110 may each include any computing device capable of executing machine-readable instructions, which may be stored on a non-transitory computer-readable medium, for example, the memory 119. By way of example, the processor 112, the calibration module 114, the PWM module 116, and the monitoring and adjustment module 118 may each include an integrated circuit, a microchip, a computer, a memory, and/or any other computer processing unit operable to perform calculations and logic operations required to execute a program. As described in greater detail herein, processor 112, the calibration module 114, the PWM module 116, and the monitoring and adjustment module 118 may each be configured to perform one or more operations in accordance with the instructions stored on the memory 119. The processor 112, the calibration module 114, the PWM module 116, and the monitoring and adjustment module 118 may be communicatively coupled to the actuators 130, the electric pulse generator 132, and the energy measurement assembly 134 in order to facilitate the generation and output of laser pulses by the laser assembly 140.

Still referring to FIG. 1, the calibration module 114 may include executable instructions or algorithms that allow the medical laser system 100 to, for example, calibrate the laser pulses generated by the laser assembly 140. The PWM module 116 may include executable instructions or algorithms that allow the PWM module 116 to, for example, generate and transmit PWM control signals to the electric pulse generator 132. The monitoring and adjustment module 118 may include executable instructions or algorithms that allow the monitoring and adjustment module 118 to, for example, monitor and adjust laser pulses based on one or more signals received from the energy measurement assembly 134 and an energy-sensing device 152. In one embodiment, the measurement assembly 134 and the energy-sensing device 152 may be integrated and provided on a single substrate or board. The combination of the measurement assembly 134 and the energy-sensing device 152 may be referred to as an energy measurement board (EMB) hereinafter. The electric pulse generator 132 may generate electric pulses based on one or more signals received from the controller (e.g., signals generated by processor 112, calibration module 114, PWM module 116, monitoring and adjustment module 118, etc.) and transmit the generated electric pulses to one or more laser cavities for generating laser (or optical) pulses.

Still referring to FIG. 1, the laser assembly 140 may include one or more laser cavities 141A-D, each laser cavity being configured to output a laser pulse (or laser beam). Each of the one or more laser cavities 141A-D includes a high reflecting window 149A-D at a proximal end, an output coupler window 146A-D at a distal end, and a chromium thulium holmium-doped YAG (CTH:YAG) laser rod 148A-D disposed between a respective high reflecting window 149A-D and an output coupler window 146A-D. A single laser cavity (e.g., laser cavity 141A, 141B, 141C, or 141D) may produce each laser pulse having a pulse wavelength of, for example, approximately 2 µm, and a pulse width in the range of 100 microseconds to a few milliseconds. With a single laser cavity, the laser assembly 140 may operate on a repetition frequency (or rate) at approximately 5 Hertz (Hz) to 20 Hz, and the maximum average power output may be approximately 30 Watts. Since the maximum laser pulse energy capable of being generated by a laser cavity decreases with an increase in the operating repetition frequency of the laser cavity, multiple laser cavities may be utilized to achieve greater average power output at relatively higher repetition frequencies (e.g., approximately 20 Hz to 80 Hz). For example, to ablate tissue and to create a high enough heat to destroy objects, such as kidney stones, it may be necessary to increase the repetition frequency of an output laser pulse by utilizing multiple laser cavities. That is, controller 110 may excite each of the multiple laser cavities 141A-D at different times and may rotate rotating mirror 142 in a synchronized manner to match each laser pulse generated by the one or more laser cavities 141A-D. As such, each laser pulse generated by each laser cavity may be combined to produce an output laser pulse having an overall repetition rate of up to approximately 80 Hertz, yielding maximum average power that may be greater than 100 Watts.

Still referring to FIG. 1, each CTH:YAG laser rod 148A-D may generate a laser pulse for each of the laser cavities 141A-D, which is directed to a corresponding relay mirror 144A-D along a laser path (e.g., a laser path A, B, etc.). Each laser pulse is reflected from a respective one of the relay mirrors 144A-D to the rotating mirror 142 (e.g., a Galvo mirror) along respective laser paths. The rotating mirror 142 may be configured to rotate about an axis based on one or more control signals received, for example, from the actuators 130, to face each of the relay mirrors 144A-D and to receive the laser pulses generated by each laser cavity 141A-D. The rotating mirror 142 may reflect each laser pulse from the laser cavities 141A and 141B along with a laser path C to a beam splitter 150 and a beam combiner 154. In one embodiment, the beam splitter 150 may split the laser pulse received via the rotating mirror 142 and transmit a portion of the laser pulse to the energy-sensing device 152.

The energy measurement assembly 134 may receive the pulse signals detected by the energy-sensing device 152 and may transmit the received pulse signals to the controller 110 for further processing. The beam combiner 154 may combine the laser pulses received from one or more laser cavities 141A-D via the rotating mirror 142. The beam combiner 154 may have a high transmission characteristic for an output laser beam (e.g., a laser pulse having a wavelength of approximately 2.1 um) and a high reflection characteristic for an aiming beam (e.g., an aiming beam having a wavelength of approximate 0.53 um). Further, the beam combiner 154 may combine the output laser beam with the aiming beam that may be incident perpendicular to that of the output laser beam. Furthermore, the beam combiner 154 may compensate for the transverse shift of the output laser beam introduced by the beam splitter 150. The combined laser pulses may be passed along the laser path C to a coupling lens 156. The coupling lens 156 may couple the combined laser pulses to an output fiber 158 to be transmitted as an output laser pulse (or pulses) 160 to a delivery location. The coupling lens 156 may be any material suitable for coupling the laser light to output fiber 158, including but not limited to a sapphire. The coupling lens 156 may have a focal length of approximately 19 millimeters but is not limited thereto.

In one exemplary embodiment, a laser pulse from the laser cavity 141A may be reflected from the relay mirror 144A to the rotating mirror 142 along the laser path A. Similarly, a laser pulse from the laser cavity 141B may be reflected from the relay mirror 144B to the rotating mirror 142 along the laser path B. The rotating mirror 142 may synchronously reflect each laser pulse from the laser cavities 141A and 141B along with the laser path C to the beam splitter 150 and the beam combiner 154. In this example, the overall repetition frequency of the laser cavities 141A and 141B may be between approximately 10 Hz and 40 Hz. Of course, different combinations of laser cavities may be utilized to achieve a desired laser pulse output at different repetition frequencies (or rates).

Still referring to FIG. 1, the medical laser system 100 of this disclosure may generate output laser pulses having different average power levels. The average power of a laser pulse may be characterized by a repetition frequency and a pulse energy level associated with one or more laser cavities 141A-D. For various medical applications, users (or operators) may preset laser pulse energy, repetition frequency, the number of laser cavities desired to be used, etc. In one embodiment, all available average power output levels for laser pulses may be programmed and stored, for example, in memory 119. A complete spectrum of the available average power output of the system 100 may be provided in one or more discrete spectrum matrices, which may be characterized by pulse energy, overall pulse repetition rates, and average optical power. The following table shows an exemplary spectrum matrix (i.e., Pulse Energy Repetition Frequency (PRF) matrix), highlighting one example of available average power levels for given repetition frequencies and pulse energy levels.

TABLE 1.1

| | | Repetition Frequency (Hz) | | | | | | | | | | | | |
|---|---|---|---|---|---|---|---|---|---|---|---|---|---|---|
| | | 5 | 6 | 8 | 10 | 15 | 20 | 25 | 30 | 35 | 40 | 50 | 60 | 70 | 80 |
| Pulse Energy (J) | 0.2 | 1 | 1.2 | 1.6 | 2 | 3 | 4 | 5 | 6 | 7 | 8 | 10 | 12 | 14 | 16 |
| | 0.3 | 1.5 | 1.8 | 2.4 | 3 | 4.5 | 6 | 7.5 | 9 | 10.5 | 12 | 15 | 18 | 21 | 24 |
| | 0.4 | 2 | 2.4 | 3.2 | 4 | 6 | 8 | 10 | 12 | 14 | 16 | 20 | 24 | 28 | 32 |
| | 0.5 | 2.5 | 3 | 4 | 5 | 7.5 | 10 | 12.5 | 15 | 17.5 | 20 | 25 | 30 | 35 | 40 |
| | 0.6 | 3 | 3.6 | 4.8 | 6 | 9 | 12 | 15 | 18 | 21 | 24 | 30 | 36 | 42 | |
| | 0.8 | 4 | 4.8 | 6.4 | 8 | 12 | 16 | 20 | 24 | 28 | 32 | 40 | 48 | 56 | |
| | 1.0 | 5 | 6 | 8 | 10 | 15 | 20 | 25 | 30 | 35 | 40 | 50 | 60 | | |
| | 1.2 | 6 | 7.2 | 9.6 | 12 | 18 | 24 | 30 | 36 | 42 | 48 | 60 | 72 | | |
| | 1.5 | 7.5 | 9 | 12 | 15 | 22.5 | 30 | 37.5 | 45 | 52.5 | 60 | 75 | | | |
| | 1.8 | 9 | 10.8 | 14.4 | 18 | 27 | 36 | 45 | 54 | 63 | 72 | 90 | | | |
| | 2.0 | 10 | 12 | 16 | 20 | 30 | 40 | 50 | 60 | 70 | 80 | 100 | | | |
| | 2.5 | 12.5 | 15 | 20 | 25 | 37.5 | 50 | 62.5 | 75 | 87.5 | 100 | | | | |
| | 3.0 | 15 | 18 | 24 | 30 | 45 | 60 | 75 | 90 | | | | | | |
| | 3.5 | 17.5 | 21 | 28 | 35 | 52.5 | 70 | 87.5 | | | | | | | |

As shown in Table 1.1, the highlighted horizontal axis indicates the overall repetition rates of the output laser pulses generated by one or more laser cavities 141A-D, and the highlighted vertical axis indicates the pulse energy levels of output laser pulses generated by the one or more laser cavities 141A-D. An average power output level of a laser pulse may be obtained by inputting, for example, via the user interface 104, a repetition frequency, and a pulse energy level indicated in a spectrum matrix (e.g., Table 1.1). For example, in order to generate a laser pulse having an average output of 4 Watts (W), a user may input, via the user interface 104, a repetition frequency of 8 Hz and a pulse energy level of 0.5 Joules (J). In one example, in order to generate an output laser pulse having an overall repetition frequency below 10 Hz (e.g., 5 Hz, 6 Hz, 8 Hz, etc.), the controller 110 may automatically generate one or more signals to control a single laser cavity (e.g., any one of the four cavities) to generate the output laser pulse. Additionally or alternatively, controller 110 may control: two laser cavities to generate an output laser pulse having an overall repetition frequency of 10 Hz to 14 Hz; three or more laser cavities to generate output laser pulses having overall repetition frequencies of 15 Hz to 19 Hz, and four laser cavities to generate output laser pulses having overall repetition frequencies at 20 Hz or higher. Of course, the spectrum matrix may be varied based on the operating capabilities of the medical laser system 100. Further, additional spectrum matrices may be programmed or generated based on different laser applications and/or treatments.

In some embodiments, the user interface 104 may receive control inputs from a user (or an operator). The control inputs may include, for example, pulse energy data (or value), repetition frequency data (or value), and/or pulse mode data (or value) associated with the output laser pulse 160. The pulse energy data and the repetition frequency data may correspond to, for example, one or more parameters listed in one or more discrete spectrum matrices (e.g., PRF matrix is shown in Table 1.1) stored in the memory 119. The laser pulse mode data may correspond to one or more laser pulse shapes that may be generated by the medical laser system 100 of this disclosure. For example, one or more laser pulse modes may include a regular pulse, a short pulse, a long pulse, a very long pulse, a dust pulse, and a burst pulse. The PWM module 116 may generate PWM control signals to modulate electric pulse signals in order to generate laser pulses having various modes (or shapes). In one embodiment, one or more parameters associated with one or more laser pulse modes may be programmed or stored in memory 119 in order to integrate the parameters of one or more pulse modes with an existing spectrum matrix (e.g., PRF matrix).

In some embodiments, the one or more laser pulse modes may be defined as a short or long pulse with high pulse energy (e.g., approximately 3500 mJ); a short or long pulse with medium pulse energy (e.g., approximately 2000 mJ); and a short or long pulse with low pulse energy (e.g., approximate 600 mJ). In some embodiments, a sub-pulse frequency (f) and a pulse profile width (t) of a PWM control signal may be predefined for all modes of laser pulses. Thereafter, the overall electric pulse width ($\tau$) may be adjusted by a user or operator to obtain a desired laser pulse mode. Additionally, laser pulses having different pulse energy levels may be achieved by changing the pulse width ($\tau$) parameter. As discussed above, laser pulses with different pulse energy levels may have the same frequency (f) and substantially similar pulse width ($\tau$). That is, the pulse energy may be adjusted based on the change in the sub-pulse duty cycle (p) of a PWM control signal.

Figure 2:
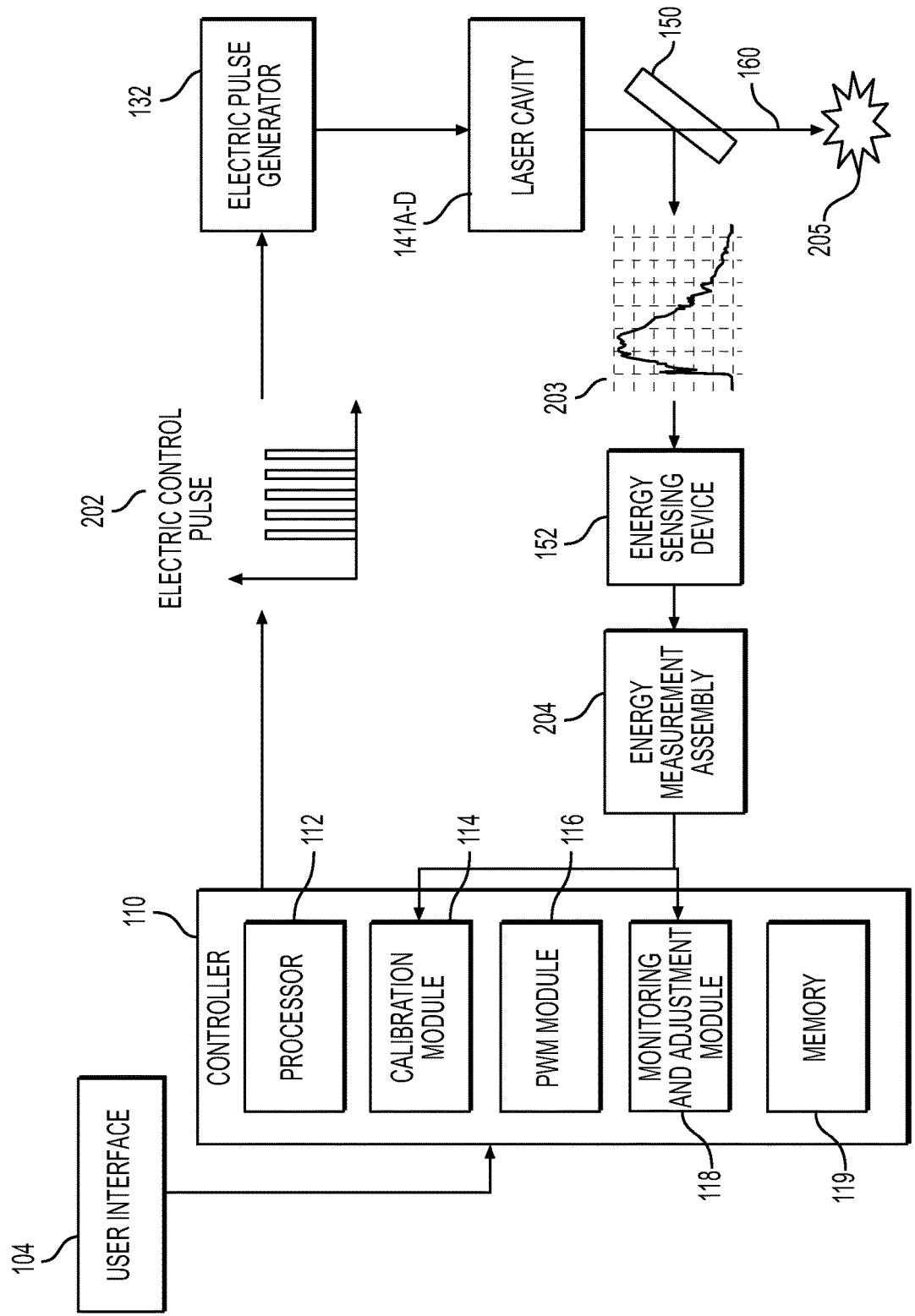
FIG. 2 illustrates an exemplary process of generating laser pulses using the medical laser system of FIG. 1, according to aspects of this disclosure.

FIG. 2 shows an exemplary laser pulse generation process 200 that utilizes techniques to calibrate and dynamically adjust laser pulses having one or more laser pulse modes (or shapes) in accordance with one or more aspects of this disclosure. In order to help ensure the accuracy of laser pulses generated by the system 100, the laser pulse energy associated with each working point (or cell) in one or more spectrum matrices (e.g., PRF matrix) should be controlled to be within a certain predetermined tolerance or threshold. In some embodiments, at least two processes may be employed singly or in combination. First, the medical laser system 100 may be calibrated. Second, the medical laser system 100 may provide a function that may dynamically adjust and control (e.g., via a closed-loop control) the laser pulse energy in response to the variations in the working states of one or more of the laser cavities 141A-D.

Still referring to FIG. 2, a user may initiate a calibration process by entering or selecting one or more inputs in the user interface 104. In one exemplary embodiment of process 200, user interface 104 may receive control inputs from a user or an operator. For example, the user may enter a request or an input to calibrate a selected laser working point (or laser mode) on one or more discrete spectrum matrices (e.g., pulse energy 0.2 J and repetition frequency of 5 Hz in the PRF matrix shown in Table 1.1) stored in the memory 119. The calibration module 114 may then generate control signals to initiate a calibration process. The controller 110 may generate an electric control pulse 202 in response to the control signals generated by the calibration module 114. The controller 110 may, for example, by utilizing the PWM module 116, the monitoring and adjustment module 118, and/or the memory 119, generate an electric control pulse 202 that may correspond to a selected laser mode (e.g., pulse energy 0.2 J and repetition frequency of 5 Hz of PRF matrix shown in Table 1.1). The electric pulse generator 132 may then generate and transmit electric pumping signals based on the electric control pulse 202 to one or more laser cavities 141A-D. The one or more laser cavities 141A-D may then generate an output laser (or optical) pulse 160 based on the electric pumping signals received from the electric pulse generator 132 to be delivered to a target site 205 (e.g., tissue of a patient) to perform, for example, a medical procedure. In some embodiments, the beam splitter 150 may split the output laser pulse 160 to reflect a portion 203 (e.g., approximately 1%) of the output laser pulse 160 to the energy-sensing device 152.

The energy sensing device 152 may respond to the received portion 203 of the output laser pulse 160 to detect and measure the energy level of the portion 203 of the output laser pulse 160. In one embodiment, the energy-sensing device 152 may detect portion 203 of the output laser pulse 160, for example, in the range of microseconds to milliseconds. The energy sensing device 152 may include a pyroelectric sensor that may detect pulse energy levels in a relatively large range, for example, approximately between 0.1 J and 5 J. The energy sensing device 152 may generate an electrical signal corresponding to the detected energy level of portion 203 of the output laser pulse 160 and transmit the electrical signal to the energy measurement assembly 204. The energy measurement assembly 204 may then perform signal transformation and signal amplification to generate a measurement signal and/or a feedback signal based on the received electrical signal that may correspond to the detected energy level of portion 203 of the output laser pulse 160. The energy measurement assembly 204 may then transmit the measurement and/or feedback signal to the calibration module 114 and monitoring and adjustment module 118 for further processing.

In some embodiments, the calibration module 114 may store one or more tables of calibrated pulse parameters based on the pulse energy level measured by the energy-sensing device 152 and the energy measurement assembly 204 (e.g., EMB) in the memory 119. For example, the following shows an exemplary table of calibrated pulse parameters.

TABLE 1.2

| Pulse Modes | 1 | 2 | 3 |
|---|---|---|---|
| Target Pulse Energy | $E_s(1)$ | $E_s(2)$ | $E_s(3)$ |
| Target EMB Measured Energy | $e_s(1)$ | $e_s(2)$ | $e_s(3)$ |
| Electric Pulse Width | $\tau_s(1)$ | $\tau_s(2)$ | $\tau_s(3)$ |

Each parameter of Table 1.2 may be defined as follows:
E=Target pulse energy;
e=Target EMB Measured pulse energy of a laser pulse; and
$\tau$=Electric pulse width corresponding to the pulse mode.
The target EMB measured pulse energy (e), and the electric pulse width (t) may be determined during a calibration process in accordance with this disclosure.

In one embodiment, a calibration process of this disclosure may be performed, for example, in a trial-and-error manner. For example, a user or an operator may operate the system 100 at a selected working point in a spectrum matrix (e.g., the PRF matrix), and adjust the pumping electric energy (e.g., by changing the electric pulse width ($\tau$)) until the output laser pulse energy level reaches the target value (e.g., within a predetermined tolerance range or threshold). The user may then record and/or store the EMB measured energy value under this condition. Additionally or alternatively, the calibration module 114 may automatically record and/or store the EMB measured energy value. A set of calibration parameters (Target pulse energy (E), target EMB measured pulse energy (e), and electric pulse width (τ)) determined based on this exemplary calibration process may be determined as the final calibrated parameters for the selected working point in the spectrum matrix. The same procedure may be performed for all working points in the spectrum matrix to calibrate the medical laser system 100. In some embodiments, for laser systems with a large number of working points (or cells) in the spectrum matrices of this disclosure, categorization of laser modes and interpolation techniques of this disclosure may be utilized (later discussed in detail).

Still referring to FIG. 2, the monitoring and adjustment module 118 may receive a measurement and/or feedback signal generated from the energy measurement assembly 204. In some embodiments, the monitoring and adjustment module 118 may perform a closed-loop control based on an algorithm or logic stored in the monitoring and adjustment module 118 and/or in the memory 119. The monitoring and adjustment module 118 may ensure the output laser pulse 160 generated by one or more laser cavities 141A-D are stable and at the required (or calibrated) level. For example, when the monitoring and adjustment module 118 receives measured pulse energy ($e_m$) from the energy measurement assembly 204, the monitoring and adjustment module 118 may perform the following closed-loop control algorithms:

1) Determine the actual energy of the laser pulse based on the measured pulse energy ($e_m$) by comparing $e_m$ with a preset target EMB measured energy $e_s(i)$:
   a) If $e_m$ is between $e_s(n)$ and $e_s(n+1)$, then calculate the actual measured energy ($E_m$) in accordance with the following algorithm:

$$E_m = \frac{E_s(n+1) - E_s(n)}{e_s(n+1) - e_s(n)} \cdot [e_m - e_s(n)] + E_s(n)$$

2) Obtain energy error value SE based on the following algorithm:

$$\delta E = E_s(m) - E_m$$

3) Determine an estimated electric pulse width error value based on the following algorithm:

$$\delta\tau = \frac{\tau_s(m+1) - \tau_s(m)}{E_s(m+1) - E_s(m)} \cdot \delta E$$

4) The estimated electric pulse width error value δτ may not be directly added to the preset electric pulse width (e.g., $\tau_s(i)$) to avoid drastic changes in pulse energy. The following damping algorithm may be applied based on a predetermined damping coefficient (g). The new adjusted pulse width delta value Δτ(new) may be determined based on the following algorithm:

$$\Delta\tau(new) = \Delta\tau_s \delta\tau \sim g$$

5) The new adjusted electric control pulse width τ(new) may be generated based on the new adjusting pulse width value in accordance with the following algorithm:

$$\tau(new) = \tau_s(i) + \Delta\tau(new)$$

Accordingly, the monitoring and adjustment module 118 may perform, by communicating, for example, with the calibration module 114 and the memory 119, the closed-control loop process (or algorithm) described above. For example, the monitoring and adjustment module 118 may dynamically adjust one or more laser pulse parameters (e.g., electric control pulse width (τ)) to output a more accurate and stabilized output laser pulse 160. That is, the closed-control loop process of this disclosure may dynamically compensate for potential laser energy shifting due to influences that may be caused by potential environmental and/or manufacturing variations.

Figure 3:
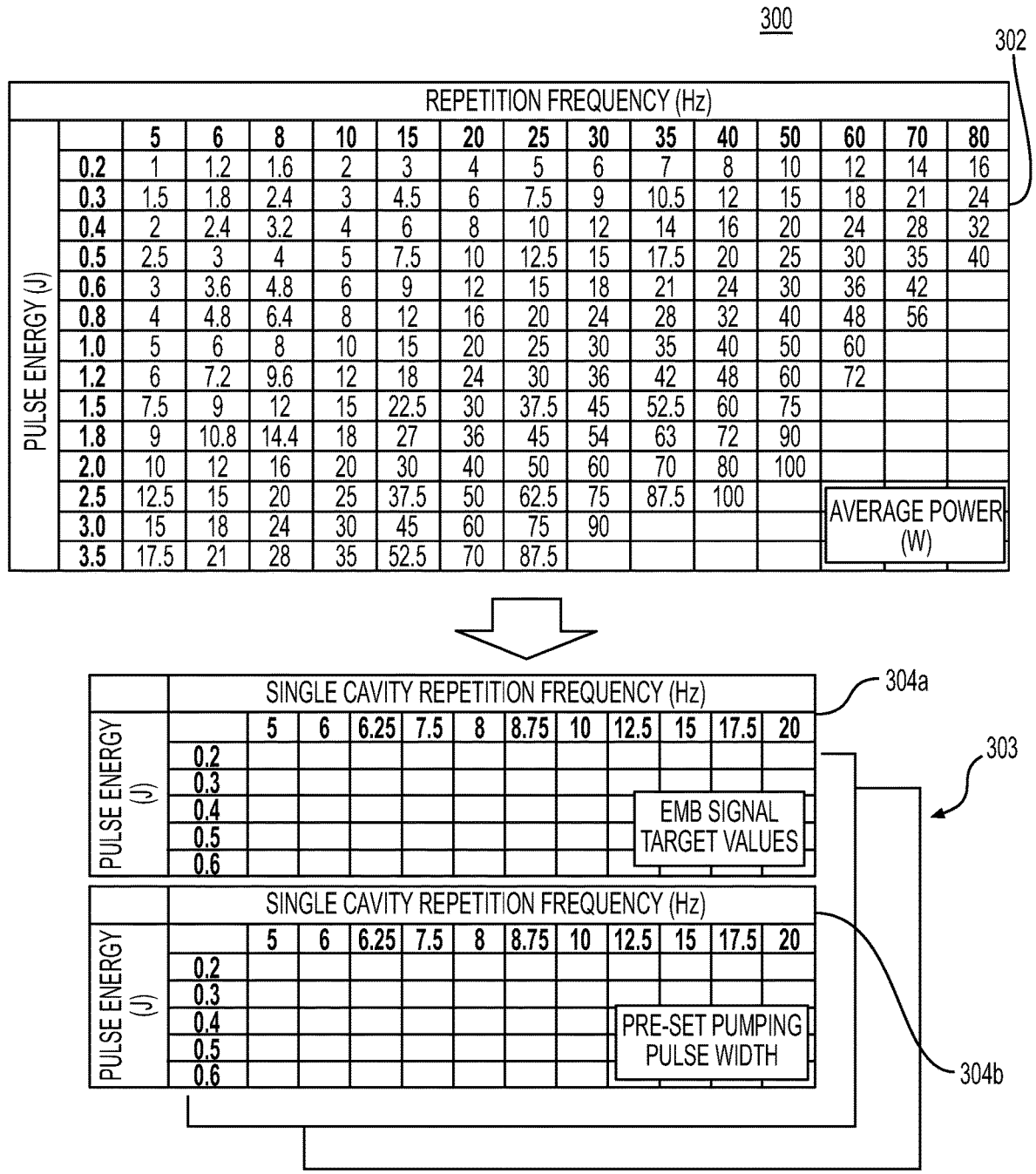
FIG. 3 illustrates an exemplary method of calibrating the laser pulses using the laser system of FIG. 1, according to aspects of this disclosure.

FIG. 3 shows an exemplary process 300 for utilizing laser pulse mode categorization techniques in accordance with the system and process disclosed in FIGS. 1 and 2. This exemplary process may allow the medical laser system 100 to be calibrated faster in a simplified manner by employing the laser pulse mode categorization techniques described hereinafter.

In some embodiments, the medical laser system 100 may include, for example, at least four laser cavities (e.g., laser cavities 141A-D). The coordinated operations performed by the four laser cavities, singly or in combination, may produce output laser pulses with pulse energy levels and repetition rates as listed in a spectrum matrix 302 (e.g., PRF Matrix table). The actual pulse repetition rate that each individual laser cavity must operate for a specific working point (or cell) may be different based on the pulse repetition rates. For example, the table below shows the operating repetition rates of the medical laser system 100 in accordance with the spectrum matrix 302, the number of cavities used for each repetition rate, and the corresponding single cavity repetition rate.

TABLE 1.3

| Repetition Rate (Hz) | 5 | 6 | 8 | 10 | 15 | 20 | 25 | 30 | 35 | 40 | 50 | 60 | 70 | 80 |
|---|---|---|---|---|---|---|---|---|---|---|---|---|---|---|
| Number of Cavities | 1 | 1 | 1 | 2 | 3 | 4 | 4 | 4 | 4 | 4 | 4 | 4 | 4 | 4 |
| Single Cavity Repetition Rate (Hz) | 5 | 6 | 8 | 5 | 5 | 5 | 6.25 | 7.5 | 8.75 | 10 | 12.5 | 15 | 17.5 | 20 |

Since each laser cavity must operate at the above-referenced single cavity repetition rates based on the output laser pulse repetition rate, the system 100 may be calibrated at a single laser cavity basis. In accordance with the embodiments of this disclosure, categorized calibration tables 303 may be established or generated based on the spectrum matrix 302. For example, the output laser parameters of the spectrum matrix 302 may be categorized into several smaller groups: short-low pulses (i.e., short pulse profile shape with low pulse energy), long-low pulses (i.e., long pulse profile shape with low pulse energy), short-medium pulses, long-medium pulses, short-high pulses, long-high pulses, dust pulses, and burst pulses. This categorization may allow different pulse features (e.g., pulse shape, pulse width, and modulation status) to be defined in different laser pulse mode groups. Further, the control resolution of the output pulse energy levels may be different based on the teaching laser pulse mode. Accordingly, multiple categorized calibration tables 303 may be generated in accordance with the calibration process of this disclosure.

In one embodiment, regular-low pulse calibration tables 304a and 304b may be generated in accordance with the calibration techniques of this disclosure. For example, a user or an operator may operate the system 100 at a selected working point (e.g., pulse energy of 0.2 J and single cavity repetition frequency 5 Hz) for a single laser cavity on the regular-low pulse calibration tables 304a and 304b. The user may then adjust the pumping electric energy (e.g., by changing the electric pulse width ($\tau$)) until the output laser pulse energy reaches the target value (e.g., within a predetermined tolerance range or threshold, for example, within approximately +/−5% of the target pulse energy). Thereafter, the user may record and/or store the EMB measured energy value under this condition. The regular-low pulse calibration tables 304a and 304b may then be populated with a set of parameters (e.g., EMB signal target values (e) and preset pumping pulse width ($\tau$)) determined based on the EMB measured energy values. In one embodiment, the categorized calibration tables 303 may be populated manually by a user by entering the calibration data into the user interface 104. Additionally or alternatively, the categorized calibration tables 303 may be populated automatically by the calibration module 114 in accordance with one or more logic or algorithms for populating or generating the categorized calibration tables 303. In one embodiment, short-low pulse and long-low pulse calibration tables (not shown for brevity) may be separately generated in a similar manner as the regular-low pulse calibration tables 304a and 304b. In some embodiments, short-low laser pulses and long-low laser pulses may be generated based on, in addition to the repetition frequency and the pulse energy in the regular-low pulse calibration tables 304a and 304b, PWM control signal parameters (e.g., a sub-pulse frequency (f) and a pulse profile width (t)). In these embodiments, the calibration tables may be generated based on expanded spectrum matrices that include one or more PWM control parameters.

They are still referring to FIG. 3, the categorized calibration tables 303 may include calibration tables for regular low-pulse mode, short low-pulse mode, long low-pulse mode, regular medium-pulse mode, short medium-pulse mode, long medium-pulse mode, short high-pulse mode, long high-pulse mode, dust pulse mode, and burst pulse mode. Each of the categorized calibration tables 303 may be generated similarly to the regular low-pulse calibration tables 304a and 304b described above. In one embodiment, the regular, short, and long-medium pulse calibration tables may include, for example, pulse energy parameters in the range of 0.8 J to 2.0 J and single cavity repetition frequency parameters in the range of 5 Hz to 17.5 Hz. The regular, short, and long-high pulse calibration tables may include, for example, pulse energy parameters in the range of 2.5 J to 3.5 J and single cavity repetition frequency parameters in the range of 5 Hz to 10 Hz. The dust and burst pulse calibration tables may include, for example, pulse energy parameters in the range of 1 J to 3.5 J and a single cavity repetition frequency of 5 Hz.

As shown in the categorized calibration tables 303, two parameters (e.g., target EMB measured pulse energy (e) (or EMB signal target values) and electric pulse width ($\tau$) (or preset pumping pulse width) may be obtained for a single laser cavity during calibration of each working point (or cell) in the categorized calibration tables. However, even with the same pulse energy level, the energy signals detected by the EMB may vary from one laser cavity to another laser cavity. As such, in one embodiment, each laser cavity in the system 100 may be calibrated separately. The calibration results of this embodiment may yield an increased accuracy for system 100. In another embodiment, a single laser cavity may be calibrated and may incorporate the results of the single laser cavity into the calibration tables of the remaining laser cavities. In one embodiment, in order to reduce potential EMB signal variances due to intrinsic physical properties of the components (e.g., laser cavities 141A-D, beam splitter 150, etc.) of the system 100, additional measures may be employed.

The accuracy of the calibration parameter values in multiple cavity laser systems and processes is disclosed in FIGS. 1-3 may be improved by providing the beam splitter 150 with a relatively constant split ratio. For example, the split ratio of the beam splitter 150 may be relatively constant and not vary with one or more features of the output laser pulses, for example, the pulse energy levels, pulse widths, and/or polarization states of the output laser pulses. In some embodiments, the beam splitter 150 may split approximately 1% to 2% of the light from the output laser beam or pulse (e.g., 160) and may reflect the split portion of the output laser pulse in a direction perpendicular to the output laser pulse. However, each laser beam (or pulse) output from different cavities (e.g., one or more laser cavities 141A-D) may have slightly different polarization states and may travel in slightly different directions. As such, the monitoring (or measurement) signals may not be consistent or accurate if the split ratio of the beam splitter 150 varies based on the incident output laser beams with the different polarization states.

In some embodiments of this disclosure, an output laser beam may be incident to the beam splitter 150 at an angle of 45° (i.e., the reflected beam will be perpendicular to the main beam). The reflection of a P-polarization component (i.e., parallel to the incident plane) of an output laser beam may be different from that of an S-polarization component (i.e., perpendicular to the incident plane) of the output laser beam. Thus, the overall split ratio of the output laser beam may depend on the polarization state of the output laser beam. In some embodiments of this disclosure, all-laser cavities (e.g., laser cavities 141A-D) may share a common target signal value based on the parameters of the output laser pulse (e.g., pulse energy, pulse mode, and pulse repetition rate). As such, in some instances, the monitoring (or measured) signal variations may result between different laser cavities even if the pulse energy of the different laser cavities may be the same due to the different polarization components of the output laser beams.

In embodiments of this disclosure, a polarization-insensitive coating may be applied to the beam splitter 150 in order to improve the consistency of the split ratio of the beam splitter 150. In some embodiments, the beam splitter 150 with a polarization-sensitive coating may yield different reflection (or split) ratios for an S-polarization component of the output laser beam and a P-polarization component of the output laser beam. However, the beam splitter 150 with the polarization-insensitive coatings may yield, for example, in a specified (or selected) small wavelength range, the split ratios for both S and P-polarizations that may be in a relatively close range, for example, approximately ±0.5%. That is, the split ratio difference between the two polarizations may be minimized at the specified wavelength (e.g., 5 Hz) and may also remain small in a range near the specified wavelength. Table 1.3 shows exemplary test results of the split ratio maximum variations in the four cavities (e.g., laser cavities 141A-D) and a comparison between the beam splitter with a polarization-insensitive coating and a polarization-sensitive coating.

TABLE 1.4

| | | Polarization Insensitive Coating | | Polarization Sensitive Coating | |
|---|---|---|---|---|---|
| Pulse Mode | Pulse Energy Level (mJ) | Average Split Ratio (%) | Relative Maximum Ratio Difference (%) | Average Split Ratio (%) | Relative Maximum Ratio Difference (%) |
| Small 5 Hz | 300 | 2.50 | 1.62 | 2.74 | 14.68 |
| Medium 5 Hz | 800 | 2.55 | 6.23 | 2.77 | 8.65 |
| | 1200 | 2.38 | 8.91 | 2.69 | 16.61 |
| | 2400 | 2.37 | 6.45 | 2.8 | 12.76 |
| Large 5 Hz | 4000 | 2.59 | 2.90 | 2.84 | 5.90 |
| Dust 5 Hz | 1000 | 2.56 | 4.65 | 2.77 | 12.11 |
| | 4000 | 2.47 | 6.15 | 2.66 | 7.38 |
| Burst 5 Hz | 1000 | 2.5 | 2.81 | 2.70 | 14.21 |
| | 4000 | 2.53 | 1.82 | 2.78 | 5.97 |

In this example, Table 1.4 shows that the variations due to the influence of different laser beam polarizations may be reduced to less than 10%. Additionally, the split ratio of both S and P-polarizations of the laser beam may have a tolerance based on one or more processes of this disclosure. The tolerance may be independent of the value of the split ratio. That is, the relative split ratio variation may be made smaller by raising the target split ratio. Therefore, a higher split ratio may be specified to improve the output energy variation between the laser cavities 141A-D.

Figure 4:
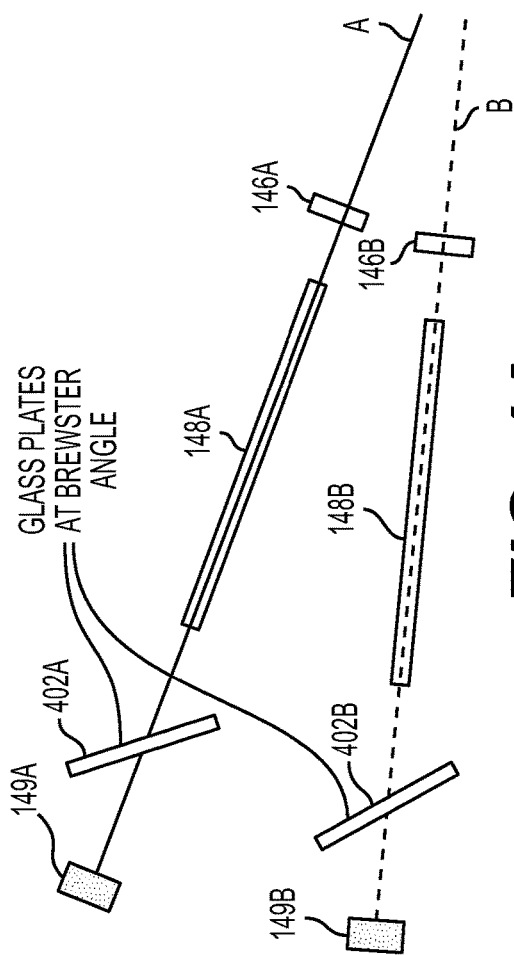
FIG. 4A illustrates exemplary laser cavities of the medical laser system of FIG. 1, according to aspects of this disclosure.
FIG. 4B illustrates an exemplary process of adjusting laser pulse using the medical laser system of FIG. 1, according to aspects of this disclosure.

Additionally or alternatively, additional optical components may be utilized to further minimize the variations in the polarization states of the laser beams generated by one or more laser cavities 141A-D. FIG. 4A shows an exemplary laser cavity that may utilize glass plate inserts 402A and 402B to minimize the variations in the polarization states of the laser beams. For example, the glass plate insert 402A may be inserted between the high reflecting window 149A and the laser rod 148A of the laser cavity 141A. Similarly, a glass plate inserts 402B may be inserted between the high reflecting window 149B and the laser rod 148B of the laser cavity 141B. Although not shown for brevity, the glass plate inserts may be inserted in a similar manner for each of the laser cavities 141A-D. In one embodiment, the glass plate inserts 402A, and 402B may be inserted inside the laser cavities 141A and 141B so as to form Brewster's angle in relation to the oscillating laser beams in the optical paths A and B. Brewster's angle (also known as the polarization angle) is an angle of incidence at which light with a particular polarization is perfectly transmitted through a transparent dielectric surface, with no reflection. In one embodiment, the glass plate inserts 402A and 402B angled at Brewster's angle may favor the P-polarization laser oscillation in the laser cavities 141A and 141B. That is, the polarization state of the output laser pulse may be controlled consistently for all laser cavities 141A-D. Accordingly, the variations of the split ratio of the beam splitter 150 may be reduced even if the beam splitter 150 may have some residual ratio difference between the two polarization directions.

Additionally or alternatively, an exemplary parameter compensation method in accordance with this disclosure may be utilized to further minimize the effects of the variations in the polarization states of the laser beams generated by one or more laser cavities 141A-D. FIG. 4B shows a parameter compensation process that may be performed by the controller 110 to compensate for the variations in the split ratios of the beam splitter 150. In one embodiment, four correction parameters may be assigned to each target measurement value ($e_s(n)$) for each laser working point (mode or cell) n in a spectrum matrix 410. The spectrum matrix 410 may include pulse energy and pulse repetition frequencies as the laser parameters. The spectrum matrix 410 may be any spectrum matrix stored or programmed in memory 119 in accordance with this disclosure and may include a complete spectrum of the available average power output of the system 100. As described in process 200 of FIG. 2, the target measured energy ($e_s(n)$) may be obtained during a calibration process of this disclosure.

Still referring to FIG. 4B, each of the four correction factor parameters (e.g., $\rho1(n)$, $\rho2(n)$, $\rho3(n)$, $\rho4(n)$) may correspond to each of the four different laser cavities 141A-D. The four correction factor parameters may be correction ratios that correspond to the measured energy ($e_m$) values for the laser cavities 141A-D, with default values being 1 for all correction factors. For example, if the measured energy ($e_m$) of a working laser point during a closed-loop control process (e.g., process 300) has errors (δE) in the actual output laser pulses based on the target measured energy ($e_s(n)$), the four correction parameters may be utilized to adjust the measured energy ($e_m$) values. In the example process shown in FIG. 4B, the target measured energy ($e_s(n)$) value for an output laser mode 416, for example, of 5 Hz and 200 mJ maybe 22.32 W. In one embodiment, a four-element correction factor table 414 may be associated with this laser mode, with default values for the four laser cavities 141A-D being 1. If the closed-loop process (e.g., process 300) results in errors (6E) in the actual output laser pulse, for example, approximately 8% above the target in the laser cavity 141A and approximately 4% below the target in cavity 141C, then the correction parameters for the laser cavities 141A and 141C may be changed to approximately 1.08 and 0.963, as shown in a four-element correction table 412. The following algorithm may be utilized to calculate the actual measured pulse energy ($E_m$) in accordance with the correction factor parameters ($\rho i(n)$) and the measured energy ($e_{(i)m}$) in the closed-loop processes as disclosed in FIG. 2:

$$E_{(i)m} = \frac{E_s(n+1) - E_s(n)}{e_s(n+1) - e_s(n)} \cdot [e_{(i)m} \cdot \rho i(n) - e_s(n)] + E_s(n)$$

The errors due to the variations between the laser cavities 141A-D may be corrected effectively by utilizing the correction parameters and the algorithm described above.

In some embodiments, the polarization-insensitive coating, the glass inserts (e.g., 402A and 402B) at Brewster's angle, and the parameter compensation method discussed above may be utilized singly or in combination to improve the accuracy of the output laser pulse measurement. For example, the accuracy requirement for the laser pulse energy may be set to be approximately within ±10% of the split ration variation. In this example, a polarization-insensitive coating may be utilized to improve the consistency of the split ratio of the beam splitter. In another example, where a higher accuracy may be required, in addition to the polarization-insensitive coating, the parameter compensation method in accordance with FIG. 4B may be utilized. In this example, the selected split ratio of the beam splitter 150 may be smaller than, for example, 1%. This example may reduce additional hardware costs. In yet another example, the polarization-insensitive coating, the glass plate inserts (e.g., 402A and 402B) arranged at Brewster's angle in relation to the laser beams, and the parameter compensation method in accordance with FIG. 4B may be utilized together in combination. In this example, consistent polarization states of the laser output from all laser cavities 141A-D may be produced.

Figure 5:
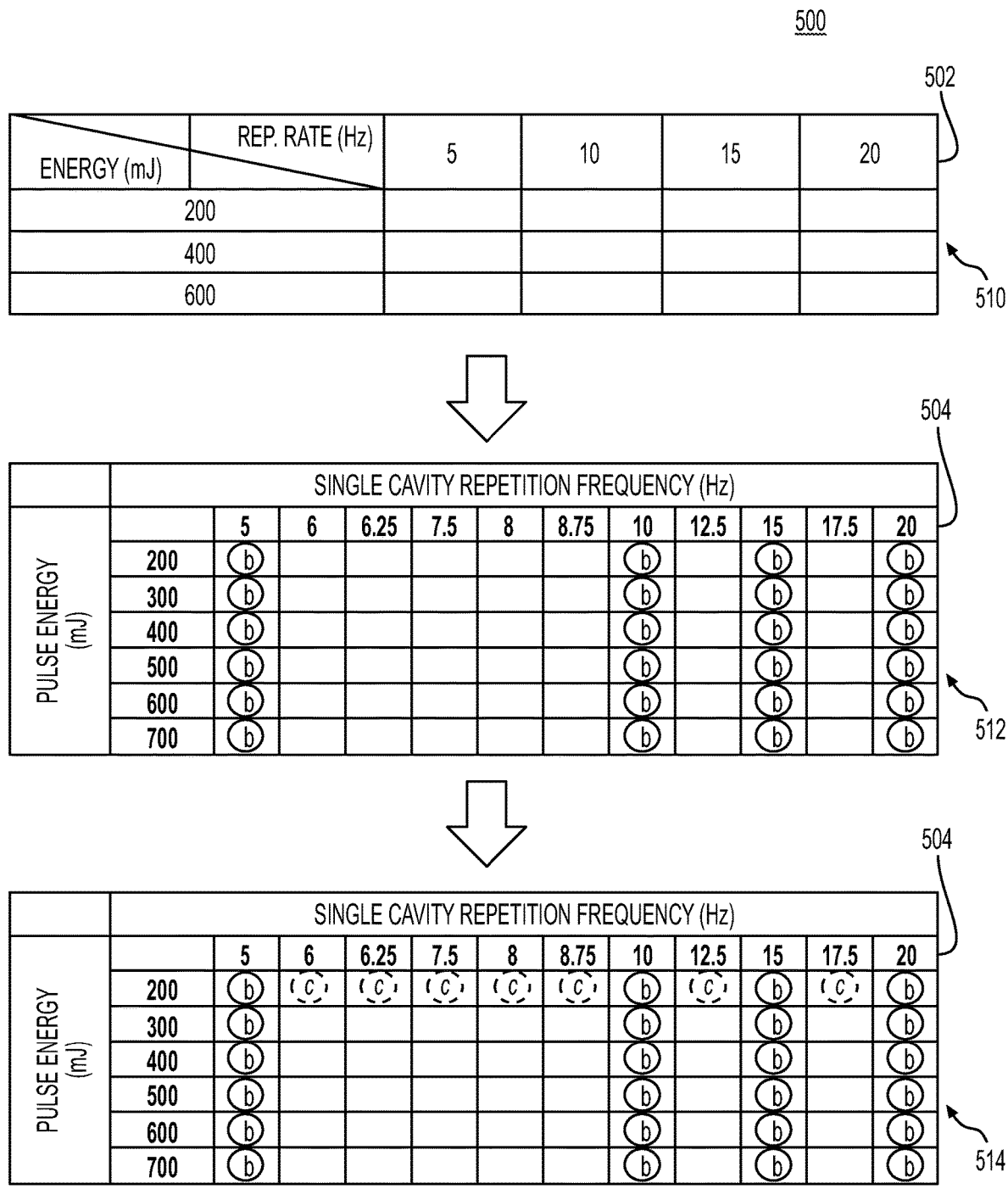
FIG. 5 illustrates an exemplary process of calibrating the energy of a laser pulse using the medical laser system of FIG. 1, according to aspects of this disclosure.

FIG. 5 shows an interpolation process 500 utilized by the calibration process performed in accordance with the system and processes disclosed in FIGS. 1-4A and 4B. The interpolation process 500 of this disclosure may reduce the amount of time required for calibrating the system 100. For example, the interpolation process 500 may calibrate the system 100 by measuring only approximately 30% (or less) of the working points of a spectrum matrix (e.g., PRF matrix) while yielding more than approximately 80% of all working points to be within the required accuracy range or threshold (e.g., a tolerance of ±5% target EMB values).

In one embodiment, a complete set of categorized calibration tables (e.g., categorized calibration tables 303) may be generated for a spectrum matrix (e.g., PRF matrix). The categorized calibration tables may be generated based on one or more laser pulse modes (e.g., regular-low pulses, short-low pulses, long-low pulses, regular-medium pulses, short-medium pulses, long-medium pulses, short-high pulses, long-high pulses, dust pulses, and/or burst pulses) of a single laser cavity. In one embodiment, the calibration parameters obtained based on the measurements of a single laser cavity (e.g., laser cavity 141A) may be utilized for generating the categorized calibration tables of the remaining laser cavities (e.g., laser cavities 141B-D). Accordingly, the calibration process in accordance with this embodiment may be performed by measuring a reduced number of working points. Additionally or alternatively, the number of working points measured may be further reduced by performing the interpolation process 500. For example, a few working points (e.g., 12) on a categorized calibration table (e.g., regular-low pulse calibration tables 304a and 304b) may be selected and measured to generate the calibrated parameters (e.g., EMB signal target values (e) and preset pumping pulse width ($\tau$)) for the entire working points on all of the categorized calibration tables.

In one embodiment, a Newtonian polynomial interpolation algorithm (or Newtonian interpolation algorithm) may be utilized to interpolate the calibrated parameters generated based on the measurements of a few selected working points on categorized calibration tables. For example, the Newtonian interpolation algorithm may be utilized to deduce, from the measurement data of the few selected working points, predicted measurement data for all working points without actually measuring each and every working point on the categorized calibration tables. In one embodiment, the Newtonian interpolation algorithm may utilize two variables, for example, x and y, that are related by a function as shown below:

$$y = f(x)$$

Assuming a set of data pairs, $\{x_i, y_i = f(x_i); I = 0, 1, 2, \ldots, n\}$ may be obtained. The value of y at position x in the range of the set of data pairs may then be approximately calculated with a certain degree of accuracy in accordance with the following interpolation algorithm:

$$\bar{y}(x) = f[x_0] + (x - x_0)f[x_0, x_1] + (x - x_0)(x - x_1)f[x_0, x_1, x_2] +$$
$$\ldots \ldots + (x - x_0)(x - x_1) \ldots (x - x_{n-1})f[x_0, x_1, \ldots, x_n]$$

Where, $$f[x_0] = y_0 = f(x_0)$$

$$f[x_0, x_1] = \frac{f[x_0] - f[x_1]}{x_0 - x_1}$$

$$f[x_0, x_1, x_3] = \frac{f[x_0, x_1] - f[x_1, x_2]}{x_0 - x_2}$$

$$\ldots \ldots$$

$$f[x_0, x_1, \ldots, x_n] = \frac{f[x_0, x_1, \ldots, x_{n-1}] - f[x_1, x_2, \ldots, x_n]}{x_0 - x_n}$$

Each function may be divided by the difference of f(x) in different orders. Since all intermediate results may be tabulated during the data collection and calculation process, numerical calculations may be performed efficiently, as shown in the following example table:

TABLE 1.5

| Collected x data | Collected f(x) data | $1^{st}$ Divided Difference | $2^{nd}$ Divided Difference | $3^{rd}$ Divided Difference |
|---|---|---|---|---|
| $x_0$ | $f(x_0)$ | | | |
| $x_1$ | $f(x_1)$ | $f[x_0, x_1]$ | | |
| $x_2$ | $f(x_2)$ | $f[x_1, x_2]$ | $f[x_0, x_1, x_2]$ | |
| $x_3$ | $f(x_3)$ | $f[x_2, x_3]$ | $f[x_1, x_2, x_3]$ | $f[x_0, x_1, x_2, x_3]$ |
| $x_4$ | $f(x_4)$ | $f[x_3, x_4]$ | $f[x_2, x_3, x_4]$ | $f[x_1, x_2, x_3, x_4]$ |

In Table 1.5, the data in the first two columns may be collected data, for example, actual measurements of laser pulses. The data in the $1^{st}$ Divided Difference column may be calculated based on the above-referenced interpolation algorithm in accordance with the collected data in the first two columns. By utilizing the results of the previous columns, the interpolation algorithm for all subsequent x values may be calculated.

In one embodiment, the Newtonian interpolation algorithm may be incorporated into the calibration process of this disclosure to interpolate the calibration parameters of the system 100. In one embodiment, each working point (or cell) of a spectrum matrix for a specified pulse mode (e.g., regular low-pulse mode) may be calibrated based, for example, on the following table:

TABLE 1.6

| | Single Cavity Repetition Frequency (Hz) | | | | | | | | | |
|---|---|---|---|---|---|---|---|---|---|---|
| | 5 | 6 | 6.25 | 7.5 | 8 | 8.75 | 10 | 12.5 | 15 | 17.5 | 20 |
| Pulse Energy (mJ) | 200 | | | | | | | | | |
| | 300 | | | | | | | | | |
| | 400 | | | | | | | | | |
| | 500 | | | | | | | | | |
| | 600 | | | | | | | | | |
| | 700 | | | | | | | | | |

In this embodiment, an additional row (e.g., 700 mJ) may be included in Table 1.6 for the purpose of performing a closed-loop control process of this disclosure. For example, in calculating a correction value of an electric pulse width of a subsequent pulse in the closed-loop control process of this disclosure, preset values for the working points with an energy level higher than the working point under adjustment may be utilized. As such, approximately calibrated parameters for the additional row (e.g., 700 mJ) may be provided for calibrating the 600 mJ pulse energy level in Table 1.6. A similar technique may be utilized for various other pulse modes. Based on Table 1.6, a reduced measurement table 502 may be derived by selecting a few working points to be measured for determining the calibration parameters.

The calibration parameter tables (e.g., the categorized calibration tables 303) generated based on the PRF matrix of this disclosure are two-dimensional (2-D). For example, the measured EMB signal values may vary with the pulse energy and/or the repetition rate of the output laser pulse. That is, an EMB signal value may be a function of two variables: pulse energy and pulse repetition rate. Thus, the interpolation process of this disclosure may be performed two-dimensionally. However, in order to reduce complexity and facilitate efficient implementation of the Newtonian interpolation algorithm, a 2-D interpolation may be decomposed into three sequential one-dimensional (1-D) interpolations. In one embodiment, the calibration parameters (target EMB measured pulse energy (e) and electric pulse width (T)) of the low-pulse mode calibration table (e.g., Table 1.6) for a single laser cavity may be determined based on the interpolation process of this disclosure. At step 510, the reduced measurement points may be selected from the regular-low pulse calibration table (Table 1.6) to generate the reduced measurement table 502. The measurement data obtained for the working points in the reduced measuring table 502 may include actual measured pulse energy value ($E_i$), measured EMB signal value ($e_i$), and pumping electric pulse width ($\tau_i$). In one embodiment, for repetition rate (F), the following table of the measured data may be generated.

TABLE 1.7

| Target Energy (mJ) | 200 | 400 | 600 |
|---|---|---|---|
| Measured Energy | $E_0(F)$ | $E_1(F)$ | $E_2(F)$ |
| Measured EMB Energy | $e_0(F)$ | $e_1(F)$ | $e_2(F)$ |
| Electric Pulse Width | $\tau_0(F)$ | $\tau_1(F)$ | $\tau_2(F)$ |

In one embodiment, the measured energy value of $E_0$ may be less than the target energy value (e.g., 200 mJ), and the measured energy value of $E_2$ may be greater than the target (600 mJ). This requirement may enable all calibrated data to be obtained by interpolation instead of extrapolation while reducing calculation errors. For example, unlike extrapolation, interpolating values of working points lying within a range covered by measured working points yields results that may be more accurate and closer to the actual measured working points than extrapolating the values of working points.

At step 512, the measured data (e.g., Table 1.7) of the working points in the reduced measuring table 502 may be utilized to determine the calibration parameters of interpolated working points (b) in an interpolation table 504. For example, interpolation calculations may be performed at each repetition rate (i.e., 5 Hz, 10 Hz, 15 Hz, and 20 Hz) in the reduced measuring table 502 to obtain all required calibration data for the working points in the interpolation table 504 at the selected repetition rates (i.e., 5 Hz, 10 Hz, 15 Hz, and 20 Hz). The interpolation calculation process may be separated into two independent calculations. One calculation process may determine the measured EMB energy values (e) for all required pulse energy levels at the measured repetition rates. For example, in the interpolation table 504, the target EMB values e(E, F) may be obtained for pulse energy levels of 200 mJ, 300 mJ, 400 mJ, 500 mJ, 600 mJ, and 700 mJ, which is a complement for closed-loop control. The interpolation calculation may be executed for repetition rates (F) at 5 Hz, 10 Hz, 15 Hz, and 20 Hz, respectively. At each repetition rate, a pair of variables (e.g., e and E) may be utilized in accordance with the following formula:

$$e = f(E;F)$$

Further, the electric pulse width (t) may be calculated based on the following formula:

$$\tau = g(E;F)$$

In accordance with the Newtonian interpolation algorithm discussed above, the intermediate parameters and the following interpolation algorithm may be determined:

$$f[E_i; F] = e_i(F), i = 0, 1, 2$$

$$f[E_0, E_1; F] = \frac{e_0(F) - e_1(F)}{E_0(F) - E_1(F)}$$

$$f[E_1, E_2; F] = \frac{e_1(F) - e_2(F)}{E_1(F) - E_2(F)}$$

$$f[E_0, E_1, E_2; F] = \frac{f[E_0, E_1; F] - f[E_1, E_2; F]}{E_0(F) - E_2(F)}$$

$$e(E; F) = e_0(F) + (E - E_0)f[E_0, E_1; F] + (E - E_0)(E - E_1)f[E_0, E_1, E_2; F]$$

In the above-derived formulas, pulse energy (E) may be an independent variable, and repetition rate (F) may be a parameter. Further, variable (i) may indicate a specific repetition rate. At a specific repetition rate, with the parameters available through measurements and calculations, and with the variable (E) taking the values of 200, 300, . . . , 700, the calibrated target EMB measured energy values (e) may be obtained for all required energy levels at a specific repetition rate (e.g., 5 Hz, 10 Hz, 15 Hz, or 20 Hz). In one embodiment, the calibrated pumping electric pulse width values at a specific repetition rate may be calculated similarly by deriving an interpolation algorithm in a similar manner described above. As such, all calibrated parameters (e.g., all target EMB values and approximate electric pulse width values) may be obtained for the repetition rates at which measurements have been performed. For example, in the interpolation table 504, (b) in the cells (or working points) may signify that the calibration parameters at the cells indicated with (b) have been obtained through the interpolation calculations in accordance with this disclosure.

At step 514, the calibration parameters of all remaining working points (or cells) in the interpolation table 504 may be determined. For example, with the parameters obtained at step 512, the interpolation calculations may be performed for the calibration parameters of the working points corresponding to different repetition rates at a specific pulse energy level in the interpolation table 504. That is, the interpolation calculations may be performed for the working points in each row of the interpolation table 504. For example, the pulse energy value may be a fixed parameter for each row, and the independent variable may now be the repetition rate (F). The intermediate parameters and the interpolation formulas for the calibration parameters having the same pulse energy may be derived as follows:

$$f[F_i; E] = e_i(E), i = 0, 1, 2, 3$$

$$f[F_0, F_1; E] = \frac{e_0(E) - e_1(E)}{F_0 - F_1}$$

$$f[F_1, F_2; E] = \frac{e_1(E) - e_2(E)}{F_1 - F_2}$$

$$f[F_2, F_3; E] = \frac{e_2(E) - e_3(E)}{F_1 - F_2}$$

$$f[F_0, F_1, F_2; E] = \frac{f[F_0, F_1; E] - f[F_1, F_2; E]}{F_0 - F_2}$$

$$f[F_0, F_1, F_2, F_3; E] = \frac{f[F_0, F_1, F_2; E] - f[F_1, F_2, F_3; E]}{F_0 - F_3}$$

$$e(E; F) =$$
$$e_0(E) + (F - F_0)f[F_0, F_1; E] + (F - F_0)(F - F_1)f[F_0, F_1, F_2; E] +$$
$$(F - F_0)(F - F_1)(F - F_2)f[F_0, F_1, F_2, F_3; F]$$

The above formulas may be implemented in the interpolation calculations to obtain the calibration parameters (e.g., calibrated target EMB energy values (e)) for all remaining working points in the interpolation table 504. For example, at the pulse energy level (E) of 200 mJ, the calibration parameters determined at step 504 (e.g., at frequencies 5 Hz, 10 Hz, 15 Hz, and 20 Hz) may be utilized to calculate the calibration parameters for the remaining working points in the row for the pulse energy level 200 mJ. For example, in the interpolation table 504, (c) in the cells (or working points) may signify that the calibration parameters have been obtained through the interpolation calculations in accordance with this embodiment. The interpolation process 500 may be repeated for the remaining pulse energy levels (e.g., 300 mJ, 400 mJ, 500 mJ, 600 mJ, and 700 mJ). Thus, the calibration parameters (e.g., calibrated target EMB energy values (e)) for all working points on the interpolation table 504 may be determined. In one embodiment, the calibrated pumping electric pulse width values (t) may be calculated similarly by deriving an interpolation algorithm similar to the interpolation algorithm described above. As such, all calibrated parameters (e.g., all target EMB values (e) and all approximate electric pulse width values (τ)) may be obtained for all pulse energy levels of the categorized calibration tables for a single laser cavity.

In one embodiment, upon completing the measurements and interpolation calculations for all pulse modes of a single laser cavity (e.g., laser cavity 141A), the calibrated parameters may be transferred to the categorized calibration tables of the remaining laser cavities (e.g., laser cavities 141B-D). The controller 110 may then utilize the calibrated parameters obtained in accordance with the interpolation techniques of this disclosure to generate one or more control signals to output calibrated laser pulses.

In some embodiments, the results of the calibration by the combination of measurements and interpolation calculations may be checked and verified. A performance test and measurements may serve as a procedure to check and verify the calibration results. The checking measurement may be performed with closed-loop control of this disclosure, which may ensure that the monitoring signal of a laser pulse energy approaches a set target. Considering the possible variations of the lasing behaviors and measurement instruments, a tolerance of ±5% may be used as a reasonable and practical accuracy requirement. The calibration process utilizing the interpolation techniques of this disclosure may enable approximately 80% of the total working points to meet the accuracy requirement. In some embodiments, the calibrated working points producing errors greater than 5%, for example, in the range of 5 to 10%, maybe adjusted individually to meet the accuracy requirement.

Figure 6:
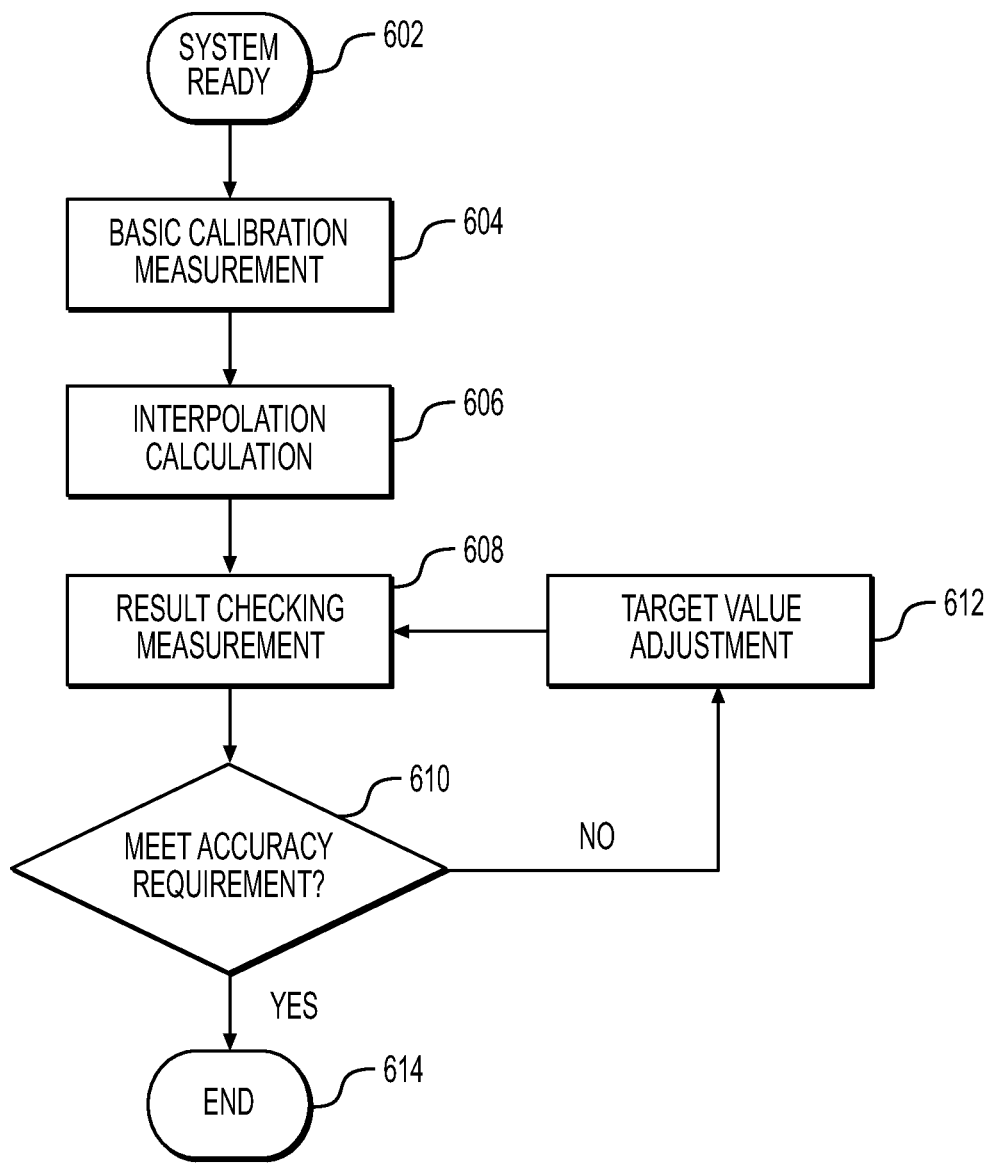
FIG. 6 illustrates a flow chart depicting an exemplary method of calibrating the laser pulses using the medical laser system of FIG. 1, according to aspects of this disclosure.

FIG. 6 shows an exemplary calibration process 600, including a closed-loop control technique in accordance with this disclosure. At step 602, the medical laser system 100 may be prepared for the calibration process of this disclosure. For example, the beam alignment of the system 100 may be performed, and the circuit parameters of the measurement assembly 134 and the energy-sensing device 152 (EMB) may be set accordingly. At step 604, an open-loop operation may be initiated by a user or an operator to collect data associated with the EMB measured values, output pulse energy, and electric pulse width at selected working points of a spectrum matrix (e.g., PRF matrix). At step 606, the calibration module 114 may utilize the measured data obtained at step 604 to interpolate the calibration parameters for all working points of the spectrum matrix of a single laser cavity (e.g., laser cavity 141A) based on the Newtonian interpolation algorithms derived in accordance this disclosure. In one embodiment, the spectrum matrix may be categorized into multiple calibration parameter tables based on one or more laser pulse modes (e.g., regular-low pulses, short-low pulses, long-low pulses, regular-medium pulses, short-medium pulses, long-medium pulses, short-high pulses, long-high pulses, dust pulses, and/or burst pulses). Further, the calibration module 114 may transfer the interpolation results of the single laser cavity to all applicable categorized calibration tables of additional laser cavities (e.g., laser cavities 141B-D) used to generate the laser pulses of the system 100. At step 608, system 100 may initiate a closed-control loop control to check the accuracy of the calibration results for all categorized calibration tables. At step 610, calibration module 114 may check whether the calibration results meet the accuracy criteria by comparing the calibration parameter values to a predetermined accuracy range or threshold (e.g., ±5% of the target pulse energy values). If the calibration parameter values are not within the predetermined accuracy range or threshold, at step 612, the calibration module 114 may adjust the EMB target values of the calibration parameter values. The calibration module 114 may then repeat the accuracy checking process until the calibration parameter values are within the predetermined range or threshold. At step 614, the calibration process 600 may end, and the system 100 may now be configured to output calibrated laser pulses for every working point on one or more laser pulse spectrum matrices in accordance with this disclosure.

In some embodiments, one or more aspects of the calibration process of this disclosure may be implemented manually. That is an independent control software or embedded instructions in the firmware of the electronic control board of the laser system 100 may be provided. Apart from the PRF matrix for operating the system 100, a set of tables may be provided for the calibration measurement operation, which may provide parameters to run the laser for measurement and record the measured results manually. Additionally or alternatively, a program may be provided to automatically conduct interpolation calculations and transfer the results to appropriate spectrum matrices or tables after the interpolation calculations are completed. In this scenario, default parameters may be preset. In some embodiments, where the calibration process is manually implemented, the user or operator may set up a pulse energy meter to measure the actual output pulse energy. The user or operator may then open the calibration tables and operate the laser at each of the working points in the calibration table, record the actual results (e.g., EMB values, actual pulse energies, etc.) in the calibration tables. After the measurement is completed, the user or operator may run the interpolation and transfer program to enter the calibration parameters in the calibration tables of the system 100. During checking and verification of the measurements, a user or operator may run all the points in the PRF matrix and check the actual output pulse energy levels. If the actual pulse energy of a working point is out of the required accuracy range or threshold, the operator may adjust the EMB target value of the point accordingly until the measured pulse energy is within the accuracy range. In one embodiment, the measurement of the output pulse energy may be integrated into the system 100 to automate the calibration process of this disclosure, and the calibration process may be conducted and controlled by control software.

Figure 7:
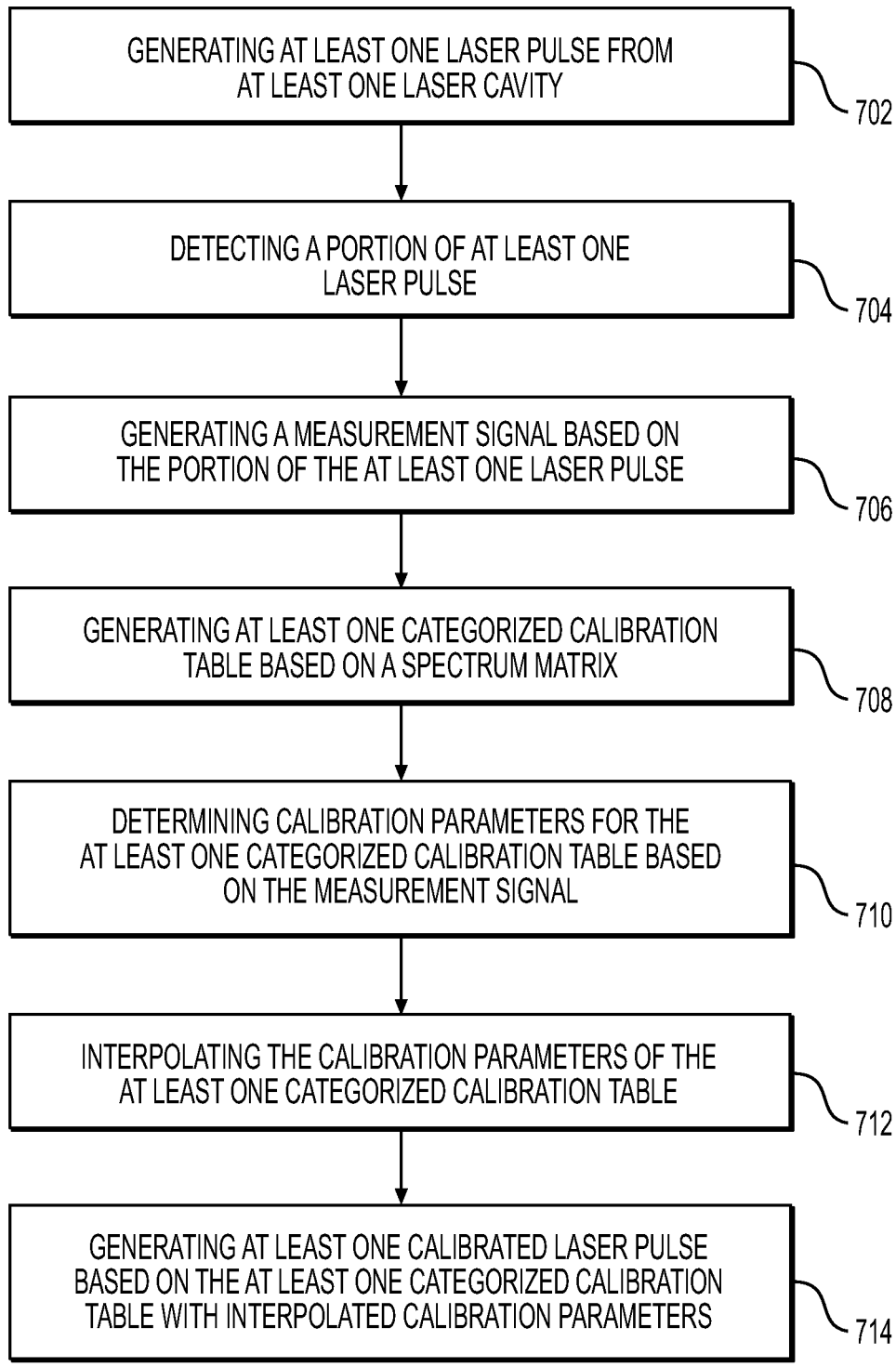
FIG. 7 illustrates a flow chart depicting another exemplary method of calibrating the laser pulses using the medical laser system of FIG. 1, according to aspects of this disclosure.

FIG. 7 shows an exemplary process 700 for calibrating the system 100 by utilizing the laser pulse mode categorization and interpolation techniques in accordance with the system and processes disclosed in FIGS. 1-6. This exemplary process may allow the system 100 to output calibrated laser pulses for medical applications or treatments on target features, such as tissues of a subject (e.g., patient).

At step 702, at least one laser cavity (e.g., laser cavities 141A-D) may generate at least one laser pulse. In one embodiment, at least one laser pulse may be generated by one of the at least one laser cavity (e.g., laser cavity 141A). At step 704, an energy-sensing device (e.g., energy sensing device 152) may detect a portion of at least one laser pulse. In one embodiment, a portion of at least one laser pulse may be reflected by the beam splitter 150. At step 706, an energy measurement assembly (e.g., energy measurement assembly 134) may generate a measurement signal based on the portion of at least one laser pulse.

At step 708, a calibration module (e.g., calibration module 114) may generate at least one categorized calibration table based on a spectrum matrix. In one embodiment, the spectrum matrix may be the PRF matrix stored in memory 119. In one embodiment, at least one categorized calibration table may be generated based on one or more laser pulse modes, the one more laser pulse modes including at least one of a regular-low pulse mode, a short-low pulse mode, a long-low pulse mode, a regular-medium pulse mode, a short-medium pulse mode, a long-medium pulse mode, a short-high pulse mode, a long-high pulse mode, a dust pulse mode, or a burst pulse mode.

At step 710, calibration module 114 may determine calibration parameters for at least one categorized calibration table based on the measurement signal. At step 712, the calibration module may interpolate the calibration parameters of at least one categorized calibration table. In one embodiment, the calibration parameters of at least one categorized calibration table may be interpolated based on a Newtonian interpolation algorithm. Further, the calibration parameters may include at least one of a target energy measurement value or a pulse width value of at least one laser pulse. In one embodiment, the interpolated calibration parameters of at least one categorization calibration table may be transferred to another categorization calibration table associated with another one of the at least one laser cavity. In one embodiment, the calibration parameters of at least one categorized calibration table may be interpolated based on one or more laser pulse energy levels and one or more laser pulse repetition rates. In one embodiment, the calibration parameters may be compared to a predetermined accuracy threshold. Further, calibration module 114 may determine whether the calibration parameters may satisfy the predetermined accuracy threshold. Upon determining the calibration parameters do not satisfy the predetermined accuracy threshold, calibration module 114 may adjust at least one of the calibration parameters. Furthermore, calibration module 114 may compare at least one of the calibration parameters to the predetermined accuracy threshold. At step 714, system 100 may generate at least one calibrated laser pulse based on at least one categorized calibration table with interpolated calibration parameters. In one embodiment, the calibrated laser pulse may be generated by one or more of the laser cavities 141A-D calibrated in accordance with the calibration techniques of this disclosure.

The medical laser system 100 of this disclosure facilitates effective and efficient calibration of output laser pulses of various modes. The calibration techniques of this disclosure reduce the number of measurements necessary to calibrate numerous working points of laser pulses on a spectrum matrix. For example, calibration measurements may be performed for a single laser cavity, and the measurement values may be interpolated to generate complete calibration parameters for multiple laser cavities. As such, calibration complexity and duration may be reduced while preventing potential errors due to inter-cavity imbalance.

It will be understood that reference is made to a number of cavities and/or mirrors in the medical laser system 100. It will be understood that the devices are not limited to this number and may change according to the requirement of the medical laser system 100. Further, while reference is made to a medical/surgical laser system, the laser pulse technique described herein is not limited to a medical/surgical laser system and may be used with any laser system.

It will be apparent to those skilled in the art that various modifications and variations may be made in the disclosed systems and methods without departing from the scope of the disclosure. It should be appreciated that the disclosed system may include various suitable computer systems and/or computing units incorporating a plurality of hardware components, such as, for example, a processor and non-transitory computer-readable medium, that allow the devices to perform one or more operations during a procedure in accordance with those described herein. Other aspects of the disclosure will be apparent to those skilled in the art from consideration of the specification and practice of the features disclosed herein. It is intended that the specification and examples be considered exemplary only.

It should be appreciated that the controller 110 in FIG. 1 may be any computing device. The user interface 104 also may include input and output ports to connect with input and output devices such as keyboards, mice, touchscreens, monitors, displays, etc. Of course, the various system functions may be implemented in a distributed fashion on a number of similar platforms to distribute the processing load. Alternatively, the systems may be implemented by appropriate programming of one computer hardware platform.

In one embodiment, any of the disclosed systems, methods, and/or graphical user interfaces may be executed by or implemented by a computing system consistent with or similar to the descriptions herein. Although not required, aspects of this disclosure are described in the context of computer-executable instructions, such as routines executed by a data processing device, e.g., a server computer, wireless device, and/or personal computer. Those skilled in the relevant art will appreciate that aspects of this disclosure can be practiced with other communications, data processing, or computer system configurations, including Internet appliances, hand-held devices (including personal digital assistants ("PDAs")), wearable computers, all manner of cellular or mobile phones (including Voice over IP ("VoIP") phones), dumb terminals, media players, gaming devices, virtual reality devices, multi-processor systems, microprocessor-based or programmable consumer electronics, set-top boxes, network PCs, mini-computers, mainframe computers, and the like. Indeed, the terms "computer," "computing device," and the like are generally used interchangeably herein and refer to any of the above devices and systems, as well as any data processor.

Aspects of this disclosure may be embodied in a special purpose computer and/or data processor that is specifically programmed, configured, and/or constructed to perform one or more of the computer-executable instructions explained in detail herein. While aspects of this disclosure, such as certain functions, are described as being performed exclusively on a single device, this disclosure may also be practiced in distributed environments where functions or modules are shared among disparate processing devices, which are linked through a communications network, such as a Local Area Network ("LAN"), Wide Area Network ("WAN"), and/or the Internet. Similarly, techniques presented herein involving multiple devices may be implemented in a single device. In a distributed computing environment, program modules may be located in both local and/or remote memory storage devices.

Aspects of this disclosure may be stored and/or distributed on non-transitory computer-readable media, including magnetically or optically readable computer discs, hard-wired or preprogrammed chips (e.g., EEPROM semiconductor chips), nanotechnology memory, biological memory, or other data storage media. Alternatively, computer-implemented instructions, data structures, screen displays, and other data under aspects of this disclosure may be distributed over the Internet and/or over other networks (including wireless networks), on a propagated signal on a propagation medium (e.g., an electromagnetic wave(s), a sound wave, etc.) over a period of time, and/or they may be provided on any analog or digital network (packet switched, circuit-switched, or other schemes).

Program aspects of the technology may be thought of as "products" or "articles of manufacture," typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives, and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical, and electromagnetic waves, such as used across physical interfaces between local devices, through wired and optical landline networks, and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

While principles of this disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

It will be apparent to those skilled in the art that various modifications and variations can be made to the disclosed system without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical laser system for outputting laser pulses, the system comprising:
   at least one laser cavity configured to generate at least one laser pulse;
   a rotating mirror configured to receive and reflect the at least one laser pulse;
   a beam splitter configured to receive and reflect a portion of the at least one laser pulse received from the rotating mirror;
   an energy-sensing device configured to detect the portion of the at least one laser pulse;
   an energy measurement assembly configured to generate a measurement signal based on the portion of the at least one laser pulse detected by the energy-sensing device; and
   a controller comprising a calibration module configured to:

generate at least one categorized calibration table based on a spectrum matrix;

determine calibration parameters for the at least one categorized calibration table based on the measurement signal;

interpolate the calibration parameters of the at least one categorized calibration table; and cause the at least one laser cavity to generate at least one calibrated laser pulse based on the at least one categorized calibration table with interpolated calibration parameters.

2. The system of claim 1, wherein the controller further comprises:

a memory comprising the spectrum matrix and the categorized calibration table.

3. The system of claim 1, wherein the at least one categorized calibration table is generated based on one or more laser pulse modes, the one more laser pulse modes including at least one of a regular-low pulse mode, a short-low pulse mode, a long-low pulse mode, a regular-medium pulse mode, a short-medium pulse mode, a long-medium pulse mode, a short-high pulse mode, a long-high pulse mode, a dust pulse mode, or a burst pulse mode.

4. The system of claim 1, wherein the calibration parameters of the at least one categorized calibration table is interpolated based on a Newtonian interpolation algorithm.

5. The system of claim 1, wherein the calibration parameters include at least one of a target energy measurement value or a pulse width value of the at least one laser pulse.

6. The system of claim 1, wherein the at least one laser pulse is generated by one of the at least one laser cavity.

7. The system of claim 6, wherein interpolated calibration parameters of the at least one categorization calibration table is transferred to another categorization calibration table associated with another one of the at least one laser cavity.

8. The system of claim 1, wherein the calibration module is further configured to:

interpolate the calibration parameters of the at least one categorized calibration table based on one or more laser pulse energy levels and one or more laser pulse repetition rates.

9. The system of claim 1, wherein the calibration module is further configured to:

compare the calibration parameters to a predetermined accuracy threshold; and determine whether the calibration parameters satisfy the predetermined accuracy threshold.

10. The system of claim 9, wherein the calibration module is further configured to:

upon determining the calibration parameters does not satisfy the predetermined accuracy threshold, adjusting the at least one of the calibration parameters; and comparing the at least one of the calibration parameters to the predetermined accuracy threshold.

11. The system of claim 1, wherein the at least one laser cavity comprises four laser cavities.

12. The system of claim 1, wherein each of the at least one laser cavity comprises a glass plate arranged at a Brewster Angle.

13. The system of claim 1, wherein the beam splitter comprises a polarization-insensitive coating.

\* \* \* \* \*